United States Patent
Fujii et al.

(10) Patent No.: US 9,719,968 B2
(45) Date of Patent: Aug. 1, 2017

(54) ULTRASOUND PROBE

(71) Applicant: KONICA MINOLTA, INC., Chiyoda-ku, Tokyo (JP)

(72) Inventors: Kiyoshi Fujii, Yokohama (JP); Manabu Migita, Yokohama (JP); Takehiko Suginouchi, Hachioji (JP)

(73) Assignee: KONICA MINOLTA, INC., Tokyo (JP)

( * ) Notice: Subject to any disclaimer, the term of this patent is extended or adjusted under 35 U.S.C. 154(b) by 207 days.

(21) Appl. No.: 14/437,077

(22) PCT Filed: Nov. 19, 2013

(86) PCT No.: PCT/JP2013/006774
§ 371 (c)(1),
(2) Date: Apr. 20, 2015

(87) PCT Pub. No.: WO2014/076973
PCT Pub. Date: May 22, 2014

(65) Prior Publication Data
US 2015/0253290 A1 Sep. 10, 2015

(30) Foreign Application Priority Data
Nov. 19, 2012 (JP) ................................ 2012-252951

(51) Int. Cl.
*G01N 29/24* (2006.01)
*A61B 8/00* (2006.01)

(52) U.S. Cl.
CPC .......... *G01N 29/24* (2013.01); *A61B 8/4455* (2013.01); *A61B 8/4461* (2013.01);
(Continued)

(58) Field of Classification Search
CPC .............................. G01N 29/24; A61B 8/4483
(Continued)

(56) References Cited

U.S. PATENT DOCUMENTS

2006/0191344 A1  8/2006  Hashimoto et al.
2009/0034370 A1* 2/2009  Guo ..................... B06B 1/0622
                                                        367/180

FOREIGN PATENT DOCUMENTS

JP    08182094 A    7/1996
JP    10094540 A    4/1998
(Continued)

OTHER PUBLICATIONS

International Search Report (ISR) and Written Opinion (WO) dated Feb. 4, 2014 issued in International Application No. PCT/JP2013/006774.

*Primary Examiner* — John Chapman, Jr.
(74) *Attorney, Agent, or Firm* — Holtz, Holtz & Volek PC

(57) ABSTRACT

An ultrasound probe which is connected to an ultrasound diagnosis apparatus includes an acoustic element for converting an electric signal and an ultrasound to each other, an electric signal processing circuit electrically connected to the acoustic element, a case for storing the acoustic element and the electric signal processing circuit, an acoustic element board for electrically connecting the acoustic element to the electric signal processing circuit, and a partition part which is arranged to contact with the case and separates the acoustic element and the electric signal processing circuit. A space on the side of the acoustic element in the case separated by the partition part is filled with a first material having lower thermal conductivity than that of a material for forming an inner wall surface of the case. Accordingly, the heat generated by a circuit unit such as the electric signal processing circuit can be more efficiently dissipated.

21 Claims, 17 Drawing Sheets

(52) U.S. Cl.
CPC ............ *A61B 8/4483* (2013.01); *A61B 8/546* (2013.01); *A61B 8/4494* (2013.01)

(58) Field of Classification Search
USPC .......................................... 73/632; 600/459
See application file for complete search history.

(56) References Cited

FOREIGN PATENT DOCUMENTS

| | | | |
|---|---|---|---|
| JP | 2003093387 A | 4/2003 |
| JP | 2006025892 A | 2/2006 |
| JP | 2006158483 A | 6/2006 |
| WO | 2006033281 A1 | 3/2006 |

\* cited by examiner

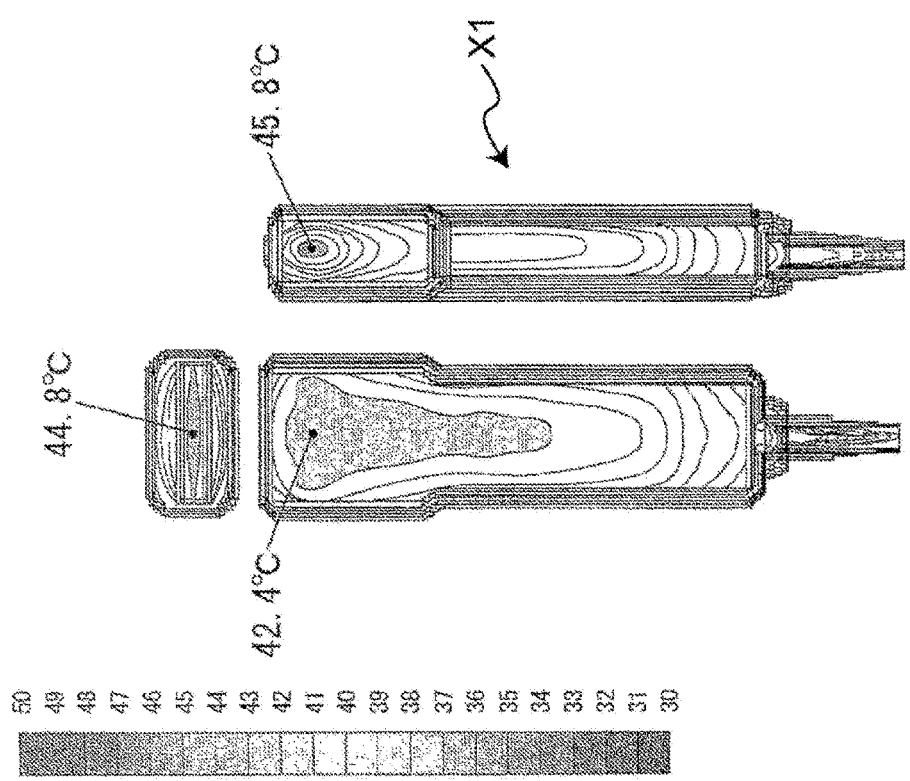

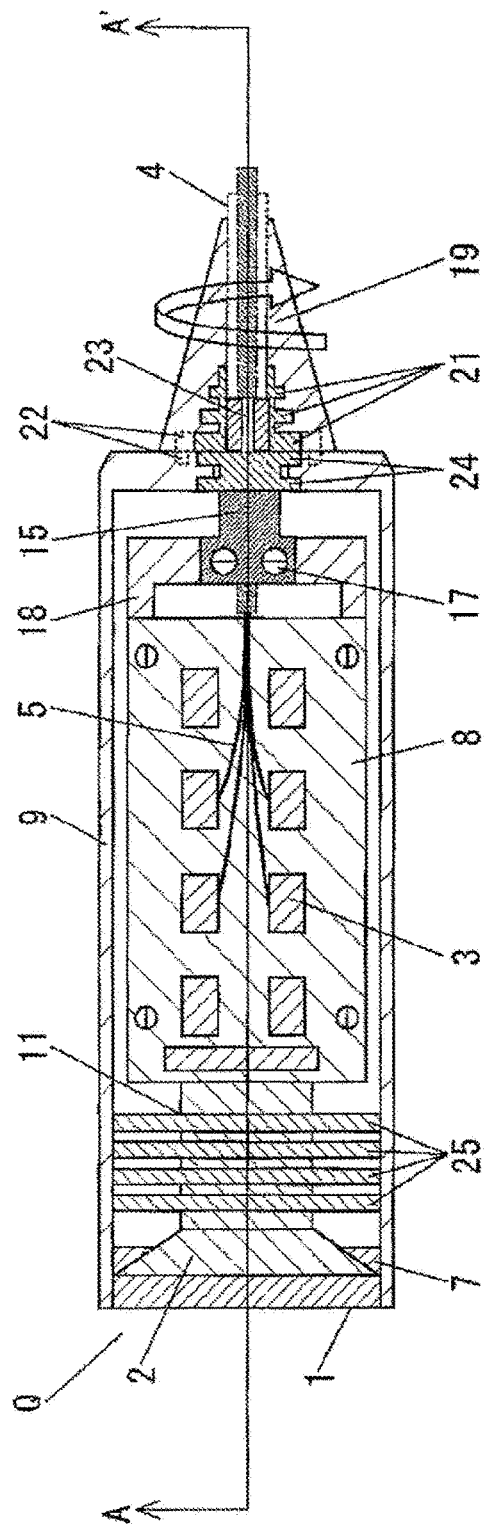
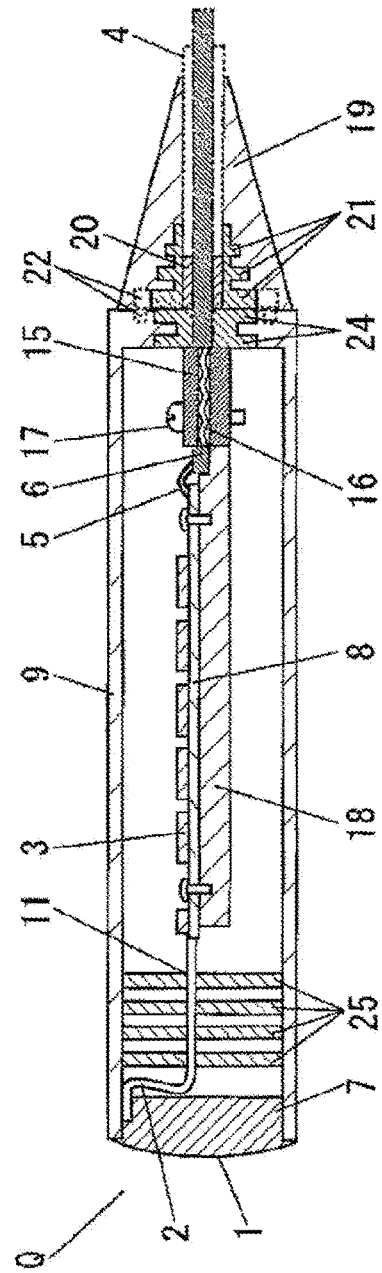
FIG. 12A
FIG. 12B

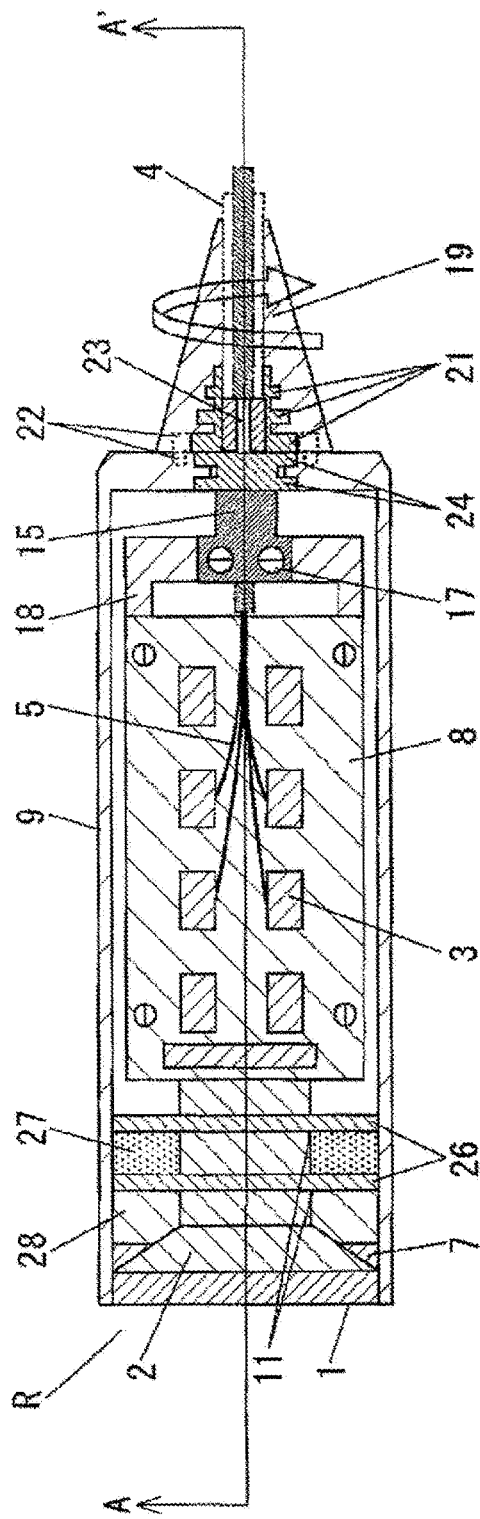
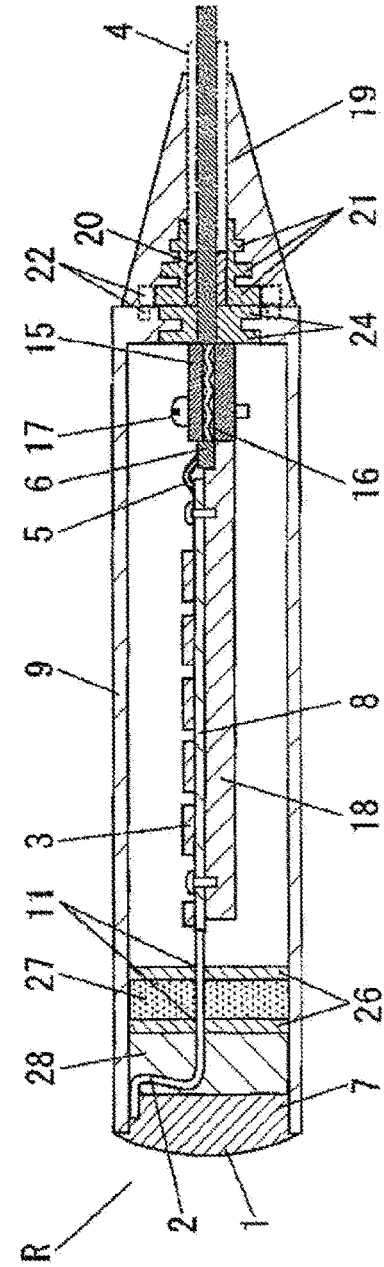
FIG. 13A
FIG. 13B

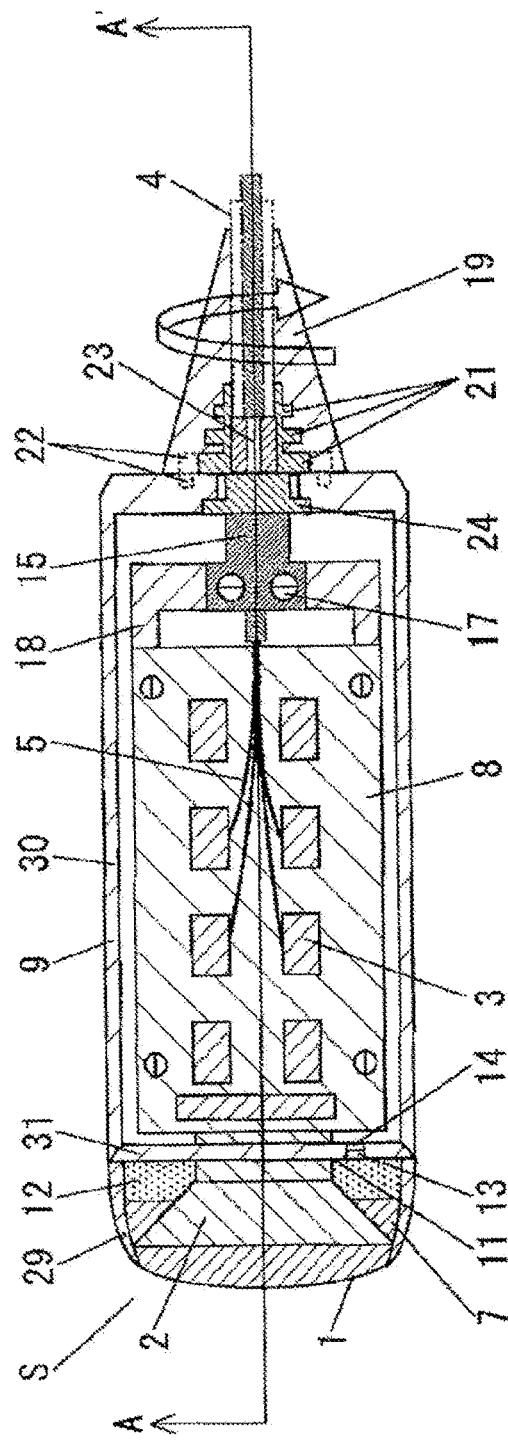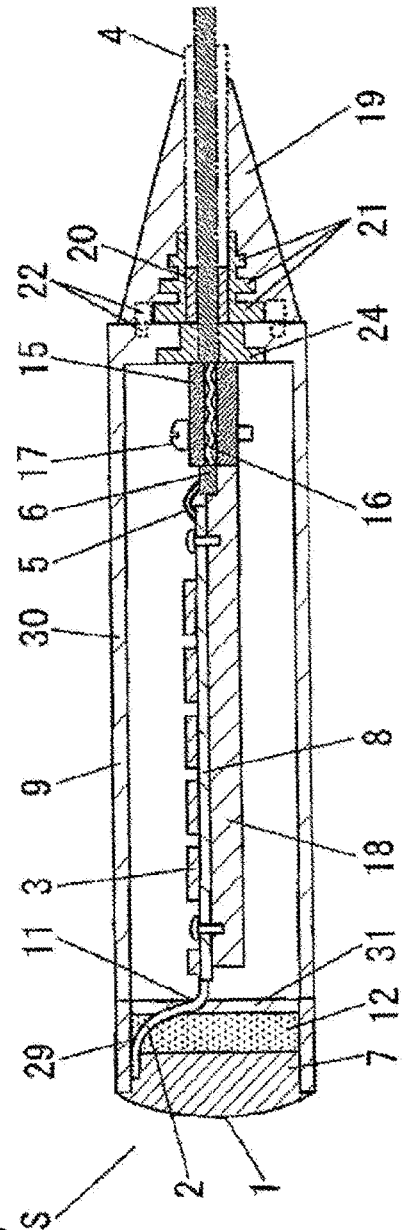
FIG. 14A
FIG. 14B

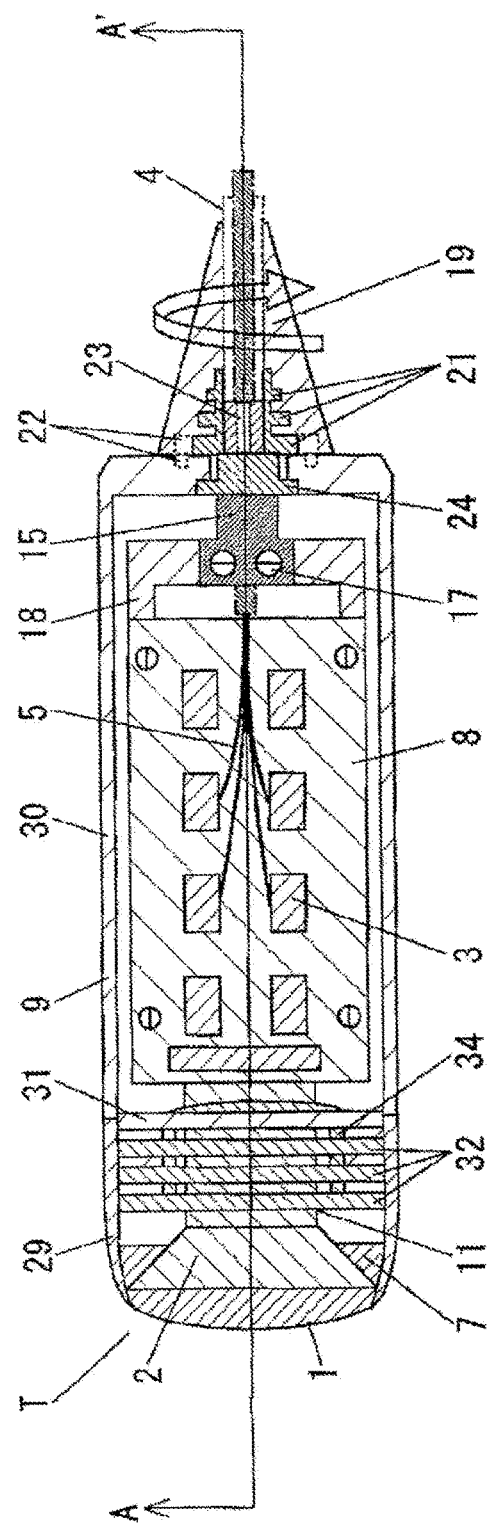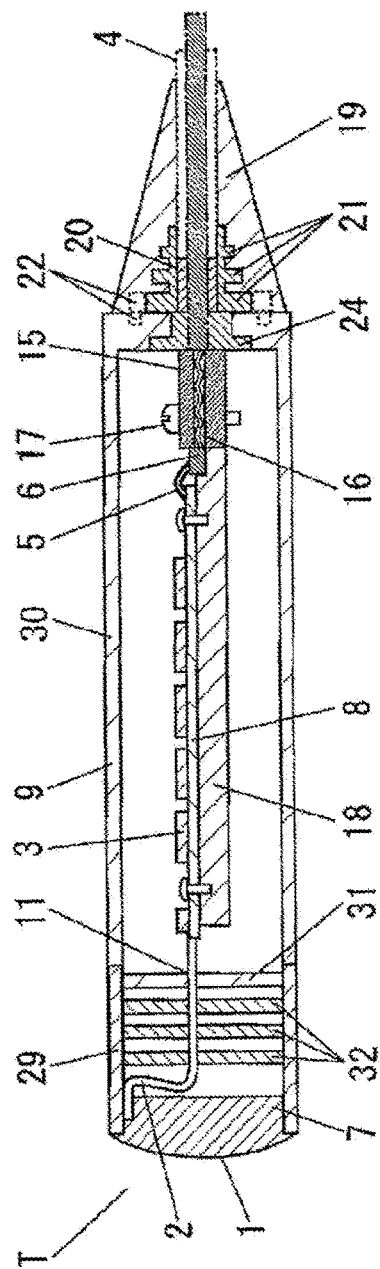
FIG. 17A
FIG. 17B

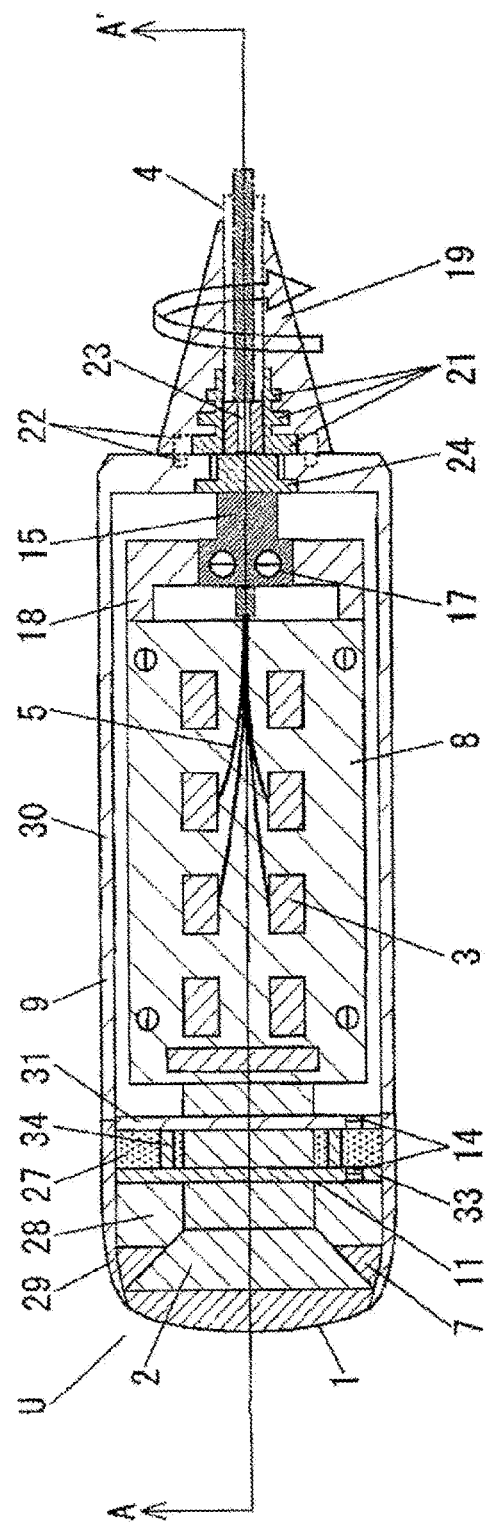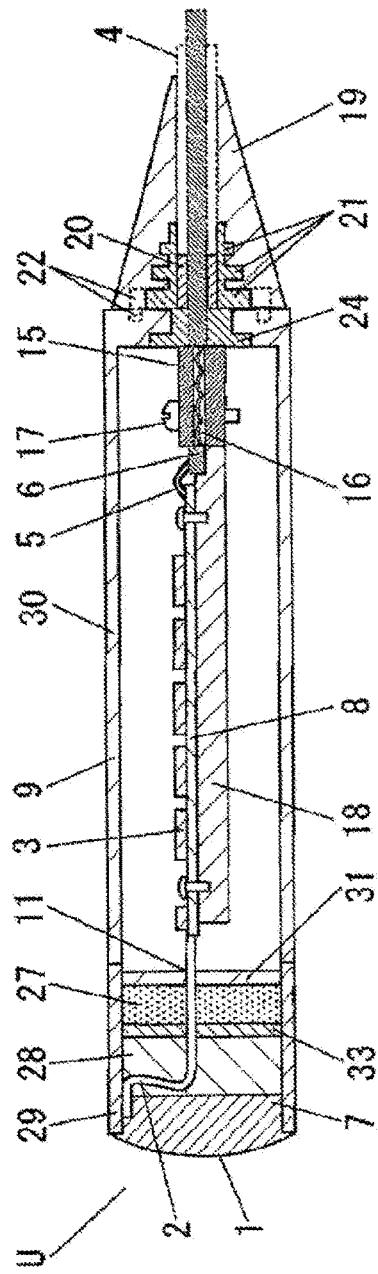
FIG. 18A
FIG. 18B

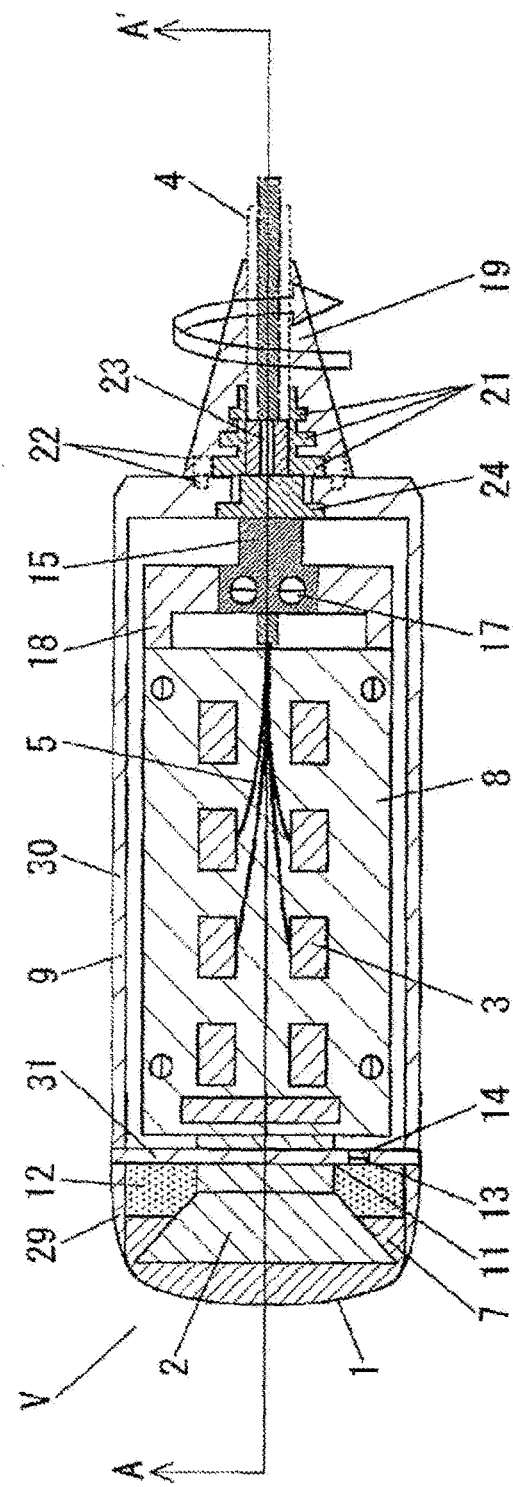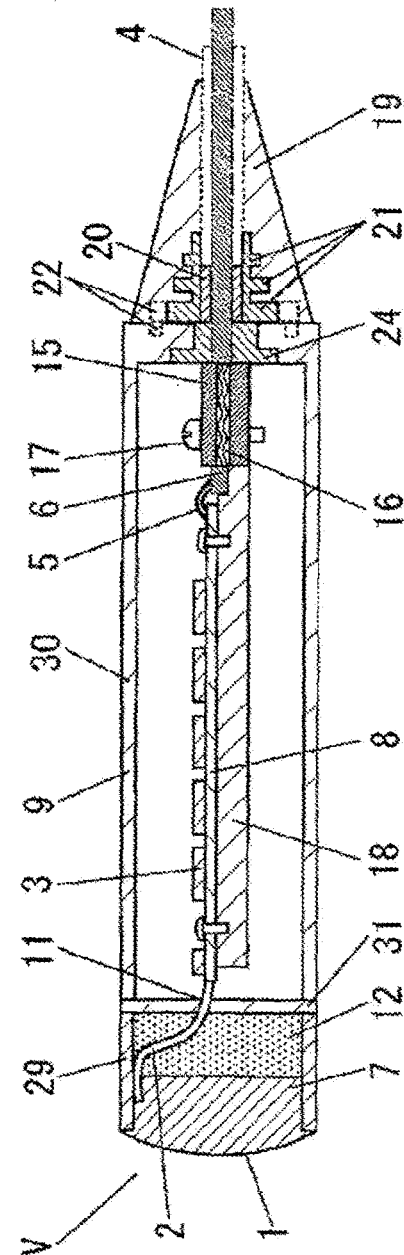
FIG. 21A
FIG. 21B

ULTRASOUND PROBE

TECHNICAL FIELD

The present disclosed technology relates to an ultrasound probe which can be used by connecting to an ultrasound diagnosis apparatus.

BACKGROUND ART

An ultrasound diagnosis apparatus for obtaining a tomographic image of a subject by transmitting an ultrasound to the subject and receiving the reflected ultrasound has been mainly used in a medical field. An ultrasound probe is connected to the ultrasound diagnosis apparatus via a connector and cable and converts an electric signal from the electric signal body into an ultrasound. The ultrasound probe Transmits the ultrasound probe to the subject as contacting with the subject, receives the ultrasound signal reflected from the subject, and converts it into the electric signal.

An acoustic element of the ultrasound probe is formed of a piezoelectric element and, for example, an acoustic matching layer, an acoustic lens, and a backing material and converts the electric signal and the ultrasound signal. The acoustic element of the ultrasound probe and the ultrasound diagnosis apparatus are connected via the cable or the connector. In recent years, in order to realize a three-dimensional display using a matrix array element, it is necessary for the acoustic element to transmit/receive significantly larger number of signals than before. It is necessary to provide cable of, for example, several thousands to transmit/receive these large number of signals between the ultrasound probe and ultrasound diagnosis apparatus via the cables. In this case, it is possible that a thicker cable reduce its usability and the cost of the cable or connector increases. In a matrix ultrasound probe which has been practically used, a subbeam former circuit is arranged in the ultrasound probe not in the ultrasound probe. Accordingly, the number of cables or connecters for transmitting/receiving the signals is reduced. Also, in order to improve a performance of the ultrasound probe, an amplifier or a switching circuit may be arranged in a place closer to the acoustic element of the ultrasound probe.

On the other hand, the temperature of a contact part with the subject or a contact part with an operator in the ultrasound probe is easily increased by heat generation caused by a power applied to the acoustic element of the ultrasound probe and heat generation caused by a circuit unit arranged near the acoustic element. Therefore, the temperatures of these contact parts are regulated from the perspective of security. As described above, when a circuit is mounted in the ultrasound probe, a problem occurs that the temperature of the acoustic element of the ultrasound probe or a housing is increased by the heat generation caused by power consumption of the circuit mounted in the ultrasound probe.

For example, an ultrasound probe disclosed in Patent Literature 1 has been proposed. In the ultrasound probe described in Patent Literature 1, a case 100 contains a circuit board 101 as illustrated in FIG. 22. The circuit board 101 is connected to a heat transfer plate 102 formed of a material having a high heat transfer coefficient. The heat transfer plate 102 and a shield case 103 are connected to a metal member 105 for an electromagnetic shield for covering around a cable 104 which transmits/receives the signal. The circuit board 101 has a heat spreader (not shown) for transmitting and dispersing the heat and is connected to the heat transfer plate 102. With this structure, the heat generated in the circuit board 101 is radiated. Also, in the ultrasound probe in Patent Literature 1, the shield case 103 connected to an acoustic element 106 and the heat transfer plate 102 contained in the case 100 is connected to the metal member 105 for the electromagnetic shield, and a gap between the circuit board 101 and the shield case 103 is covered with a rigid urethane foam having a high heat insulating performance. With this structure, the heat of the circuit board 101 is prevented from being transferred to the acoustic element 106.

CITATION LIST

Patent Literature

Patent Literature 1: JP 2006-25892

SUMMARY OF INVENTION

Technical Problem

However, according to the ultrasound prove described in Patent Literature 1, the heat of the circuit unit 101 cannot be sufficiently prevented from being transferred to the acoustic element 106.

In the ultrasound probe described in Patent Literature 1, the acoustic element 106 is connected to the electromagnetic shield member near the metal member 105 for the electromagnetic shield or the cable 104 via the shield case 103. Also, the heat generated from the circuit unit 101 is dissipated by connecting the circuit board 101 to the metal member 105 for the electromagnetic shield via the heat spreader and the heat transfer plate 102. With this structure, the heat collected to the metal member 105 for the electromagnetic shield or the shield case 103 near the cable 104 causes convection of air convection in a space between the case 100 and the shield case 103. Specifically, when the acoustic element 106 is held upward, there is a problem in that the temperature of the acoustic element 106 increases because the heat generated from the circuit unit 101 is transferred to the acoustic element 106.

A purpose of the present disclosed technology is to provide an ultrasound probe which includes an acoustic element for converting an electric signal and ultrasound and a circuit unit such as an electric signal processing circuit electrically connected to the acoustic element and can prevent the heat generated by the circuit unit from being transferred to the acoustic element.

Solution to Problem

In order to achieve the above object, according to the present disclosed technique, there is provide an ultrasound probe for connecting to an ultrasound diagnosis apparatus, including: an acoustic element configured to convert an electric signal and an ultrasound to each other; an electric signal processing circuit configured to be electrically connected to the acoustic element; a case configured to store the acoustic element and the electric signal processing circuit; an acoustic element board configured to electrically connect the acoustic element to the electric signal processing circuit; and a partition part configured to be arranged so as to contact with the case and separate the acoustic element and the electric signal processing circuit, wherein a space on a side of the acoustic element in the case separated by the partition part is filled with a first material having lower thermal conductivity than that of a material for forming an inner wall surface of the case.

Further, the electric signal processing circuit may contact with gas.

Further, the ultrasound probe may include: a circuit unit board configured to include the electric signal processing circuit mounted on the circuit unit board; a cable configured to electrically connect the electric signal processing circuit to the ultrasound diagnosis apparatus and transfer a signal; and at least one or more arms configured to be connected to the cable and support the circuit unit board, and the arms may have higher thermal conductivity than that of the first material.

Further, the arm may be formed of a conductive material, and the circuit unit board may include a ground electrode of the electric signal processing circuit in a contact part with the arm.

Further, the ultrasound probe may include a cable clamp configured to fix the cable, and the cable may be connected to the arm via the cable clamp.

Further, the cable clamp may be connected to a heat dissipating plate arranged to surround the cable.

Further, the cable clamp and the arm may be integrally formed.

Further, the arm may be formed of metal, and oxidation treatment or heat radiating coating may be performed to a surface of the arm on the side of the cable clamp from the center in a longitudinal direction.

Furthermore, the ultrasound probe may further include a strain relief configured to be penetrated by the cable outside the case and contact with the case, and the heat dissipating plate may include a first heat dissipating plate arranged between the case and the cable and a second heat dissipating plate arranged in the strain relief and for contacting with the first heat dissipating plate.

Further, the case may include at least a first and second parts, and the first and second parts may be bonded to each other.

Further, the first and second parts may respectively cover from the acoustic element to the electric signal processing circuit.

Further, the partition part may be integrally formed with the first part.

Further, a hole may be formed in a part positioned between the partition part and the acoustic element in the case, and an opening on the side of the acoustic element of the hole may be sealed with the first material in a state where a space on the side of the acoustic element in the case has been filled with the first material.

Further, the first part may store the acoustic element, the second part may store the electric signal processing circuit, and the first and the second parts may be bonded between the acoustic element and the electric signal processing circuit.

Further, the partition part may be formed on a plane of a bonding surface of the first and second parts.

Further, a first hole through which the acoustic element board passes and a second hole different from the first hole may be formed in the partition part, and an opening on the side of the acoustic element of the second hole may be sealed with the first material in a state where a space on the side of the acoustic element in the case has been filled with the first material.

Further, the partition part may be sandwiched between the first and second parts on the bonding surface of the first and second parts.

Further, the partition part may include at least two or more partition plates.

Further, in the at least two or more partition plates, a space between the at least two or more partition plates may be filled with the first material, and a space between the acoustic element and the partition plate may be filled with a second material with higher thermal conductivity than that of the first material.

Further, the first part may have higher thermal conductivity than that of the partition part.

Further, a graphite layer may be formed on an inner wall surface of the case.

Advantageous Effects of Invention

An ultrasound probe according to the present disclosed technique can prevent the heat generated by a circuit unit such as an electric signal processing circuit from being transferred to an acoustic element.

BRIEF DESCRIPTION OF DRAWINGS

FIG. 7A is a diagram of a calculation result of a surface temperature on the ultrasound prove in a case where air exists between the separated acoustic element and the electric signal processing circuit.

FIG. 7B is a diagram of a calculation result of a surface temperature on the ultrasound probe in a case where all the space in the case is filled with the insulation material.

FIG. 12A is a cross-sectional diagram of an exemplary ultrasound probe Q of a first modification according to the first embodiment.

FIG. 12B is a cross-sectional diagram of the exemplary ultrasound probe Q in FIG. 12A viewed from an A-A' cross section.

FIG. 13A is a cross-sectional diagram of an exemplary ultrasound probe R of a second modification according to the first embodiment.

FIG. 13B is a cross-sectional diagram of the exemplary ultrasound probe R in FIG. 13A viewed from an A-A' cross section.

FIG. 14A is a cross-sectional diagram of an exemplary ultrasound probe S according to a second embodiment.

FIG. 14B is a cross-sectional diagram of the exemplary ultrasound probe S in FIG. 14A viewed from an A-A' cross section.

FIG. 17A is a cross-sectional diagram of an exemplary ultrasound probe T of a first modification according to the second embodiment.

FIG. 17B is a cross-sectional diagram of the exemplary ultrasound probe T in FIG. 17A viewed from an A-A' cross section.

FIG. 18A is a cross-sectional diagram of an exemplary ultrasound probe U of a second modification according to the second embodiment.

FIG. 18B is a cross-sectional diagram of the exemplary ultrasound probe U in FIG. 18A viewed from an A-A' cross section.

FIG. 21A is a cross-sectional diagram of an exemplary ultrasound probe V of a third modification according to the second embodiment.

FIG. 21B is a cross-sectional diagram of the exemplary ultrasound probe V in FIG. 21A viewed from an A-A' cross section.

DESCRIPTION OF EMBODIMENTS

A first and second embodiments of an ultrasound probe according to the present disclosed technique will be described below with reference to the drawings.

First Embodiment

Figures 1A, 1B:
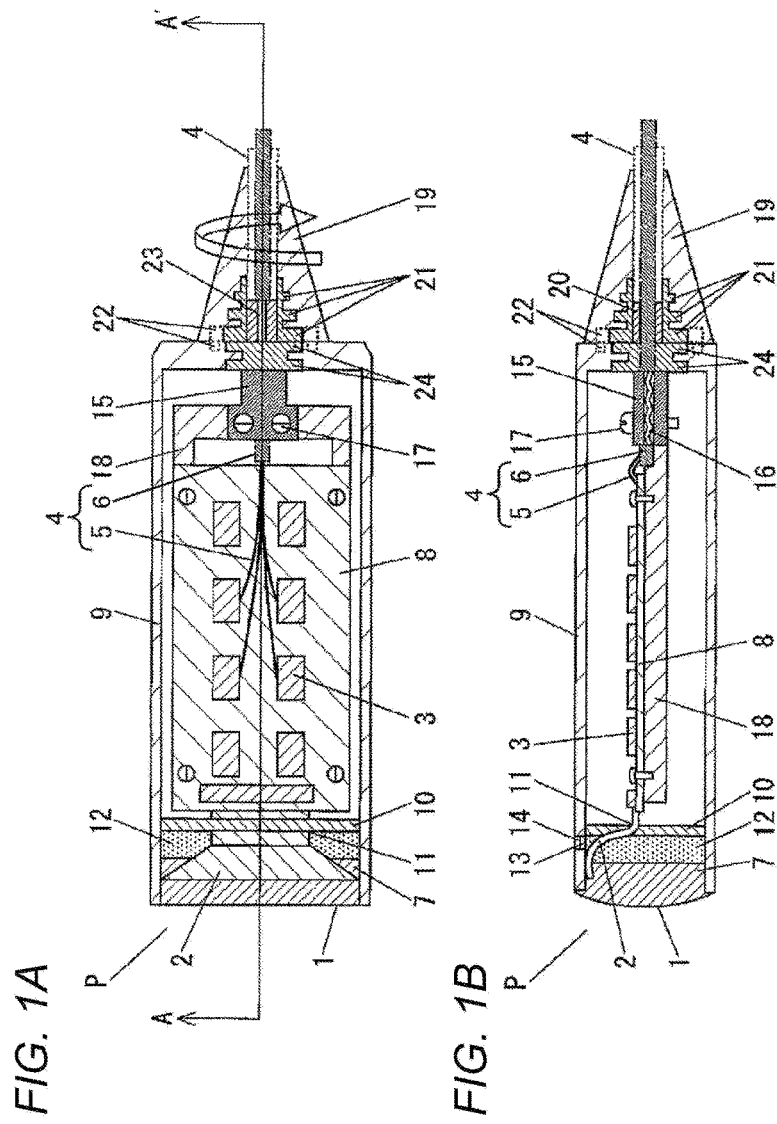
FIG. 1A is a cross-sectional diagram of an exemplary ultrasound probe P according to a first embodiment.
FIG. 1B is a cross-sectional diagram of an exemplary ultrasound probe P in FIG. 1A viewed from an A-A' cross section.

FIG. 1A is a cross-sectional diagram of a first embodiment of an ultrasound probe P according to the present disclosed technique. FIG. 1B is a cross-sectional diagram of the ultrasound probe P in FIG. 1A viewed from an A-A' cross section. FIGS. 1A and 1B are diagrams of an exemplary ultrasound probe according to the present disclosed technique.

An acoustic element 1 converts an electric signal and an ultrasound signal. The acoustic element 1 is connected to an acoustic element board 2 and electrically connected to an electric signal processing circuit 3 via the acoustic element board 2. The electric signal processing circuit 3 is electrically connected to a cable 4 and electrically connected to an ultrasound diagnosis apparatus which is not shown via the cable 4 and a connector (not shown). According to this, one end of an ultrasound probe P can be connected to the ultrasound diagnosis apparatus which is not shown via the cable 4 and the like.

The cable 4 includes a signal line 5 and a cable shield 6 for covering an outer surface of the signal line 5. The signal line 5 electrically connects the electric signal processing circuit 3 and the ultrasound diagnosis apparatus to each other. A transmission signal from the ultrasound diagnosis apparatus is transferred to the acoustic element 1 via the electric signal processing circuit 3. Accordingly, an ultrasound is transmitted from the acoustic element 1 to a subject. The transmitted ultrasound is reflected by the subject. The acoustic element 1 converts the ultrasound reflected by the subject into the electric signal. The electric signal processing circuit 3 performs signal processing to the electric signal. The electric signal processed by the electric signal processing circuit 3 is transferred to the ultrasound diagnosis apparatus via the cable 4. Accordingly, an ultrasonic diagnosis image is displayed on a display and the like connected to the ultrasound diagnosis apparatus. The acoustic element 1 includes at least a piezoelectric element. In the first embodiment, the acoustic element 1 further includes an acoustic matching layer, a backing material 7, an acoustic lens, and the like.

Here, since a part of the energy of the transmission signal from the ultrasound diagnosis apparatus becomes the heat in the acoustic element 1 of the ultrasound probe P, the temperature of the acoustic element 1 increases.

The electric signal processing circuit 3 is mounted on a circuit unit board 8. The electric signal processing circuit 3 includes a transmission drive circuit, a changeover switch, an amplifier circuit of a reception signal, a circuit for delaying and adding the reception signal, and the like. In the electric signal processing circuit 3, a circuit for performing the signal processing to the transmission signal from the ultrasound diagnosis apparatus or a circuit for performing the signal processing to the reception signal from the acoustic element 1 is integrated. In a process for transmitting/receiving the signal in the circuits, the electric signal processing circuit 3 generates the heat.

The case 9 stores the acoustic element 1 and the electric signal processing circuit 3. The "storage" includes a case where the acoustic element 1, which is an object, is partially, not wholly, stored as illustrated in FIGS. 1A and 1B. The case 9 is separated into two parts, i.e., an upper part and a lower part (first and second parts). The parts of the case 9 are bonded to each other so as to cover both the acoustic element 1 and the electric signal processing circuit 3. That is, each part of the case 9 is bonded with an adhesive and the like so as to cover from the acoustic element 1 to the electric signal processing circuit 3. With this bond, the components such as the acoustic element 1, the acoustic element board 2, and the electric signal processing circuit 3 are stored in the case 9.

The case 9 is preferably formed of a material having insulation properties and high heat conductivity. For example, the case 9 is formed by mixing a resin such as a PBT resin, a PPS resin, a nylon resin, and a phenol resin with a filler such as silicon carbide, silicon carbide, aluminum nitride, boron nitride, magnesium oxide, aluminum oxide, and aluminum nitride. These materials have high thermal conductivity of 2 to 15 W/m·K and also have the insulation properties. The heat can be dispersed to the whole case 9 by using these high heat conductive materials as a material of the case 9. According to this, a state where the temperature of a specific part of the case 9 increases can be prevented. Also, when at least an inner surface (side where the acoustic element 1 and the like is stored) of the case 9 has high thermal conductivity, the increase in the temperature of the specific part of the case 9 can be prevented regardless of the degree of the heat conductivity of the outer side of the case 9. Therefore, a layer of the material with high thermal conductivity may be formed on the inner surface of the case 9. For example, graphite may be coated on the inner surface of the case 9 as the material with high thermal conductivity. The layer of the material with high thermal conductivity may be formed on the side of the electric signal processing circuit 3 on the inner surface of the case 9, it is not necessary to form the layer of the material with high thermal conductivity on the side of the acoustic element 1. With this structure, while the heat generated from the electric signal processing circuit 3 is dispersed to the case 9, the heat can be prevented from being dispersed to the side of the acoustic element 1.

A partition part 10 for spatially separating the acoustic element 1 and the electric signal processing circuit 3 is provided in one part of the case 9. In the first embodiment, the partition part 10 is integrally formed with one part of the case 9. However, the structure is not limited to this, and the partition part 10 which is separately formed from the case 9 may be provided in the case 9. An outer surface of the case 9 is not separated by the partition part 10 and covers from the acoustic element 1 to the processing circuit 3. The partition part 10 is arranged so as to contact with an inner surface of another part of the case 9.

A through-hole 11 is provided in the partition part 10, and the acoustic element board 2 passes through the through-hole 11 so as to pass through it. For example, the acoustic element board 2 is formed of glass or epoxy resin. It is preferable that the size of the through-hole 11 be generally a size in which the partition part 10 is contacted with the acoustic element board 2. However, the size is not limited to this, and there may be a gap in which the heat transmission caused by the air convection via the through-hole 11 can be ignored. Also, the through-hole 11 may be formed by providing the partition parts 10 in each part of the case 9 and providing a notch in the part of the partition part 10 where the acoustic element board 2 passes through. Also, the partition part 10 may be integrally formed with the case 9 by using the same material as that of the case 9. The partition part 10 and the case 9 are bonded together without a gap by integrally forming the partition part 10 with the case 9. According to this, the convention of the air can be prevented between a space on the side of the acoustic element 1 in the case 9 and a space on the side of the electric signal processing circuit 3.

The space on the side of the acoustic element 1 in the case 9 separated by the partition part 10 is filled with rigid urethane foam and the like as an insulation material 12 (first material 12) with low thermal conductivity. The space on the side of the acoustic element 1 separated by the partition part 10 is a space surrounded by the acoustic element 1 and the partition part 10 in the case 9. More specifically, the above space indicates a space surrounded by the backing material 7 of the acoustic element 1 and the partition part 10 in the case 9. Since it is preferable that the insulation material 12 have thermal conductivity lower than that of at least the inner surface of the case 9, the insulation material 12 may be air. However, a solid material is preferable for the insulation material 12. In addition, the insulation material 12 may be expanded polystyrene foam, glass wool, rock wool, wood, and the like. The thermal conductivity of the insulation material 12 on the side of the acoustic element 1 is lower than that of the inner surface of the case 9 so that the heat is hardly transferred between the space on the side of the electric signal processing circuit 3 in the case 9 and the acoustic element 1. Accordingly, the transfer of the heat generated from the electric signal processing circuit 3 to the acoustic element 1 can be prevented.

When the size of the through-hole 11 is a size in which the partition part 10 does not contact with the acoustic element board 2, it is preferable to fill the gap between the partition part 10 and the acoustic element board 2 with the insulation material 12. Also, it is not necessary that all the space on the side of the acoustic element 1 separated by the partition part 10 be filled with the insulation material 12. However, it is preferable for the gap to be filled with the insulation material 12 so that the insulation material 12 adheres to both the partition part 10 and the acoustic element 1. In this way, the gap is filled with the insulation material 12, and the partition part 10 contacting with the case 9 is formed. Accordingly, the transfer of the heat generated by the electric signal processing circuit 3 to the acoustic element 1 via the acoustic element board 2 and the case 9 can be prevented.

Figure 4:
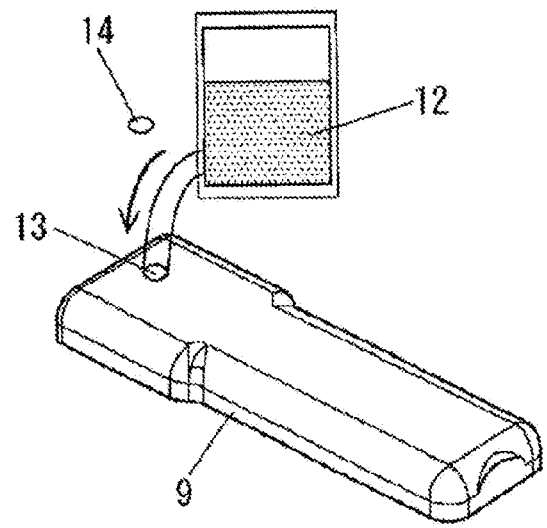
FIG. 4 is a view of an exemplary method for filling an insulation material in the case of the ultrasound probe according to the first embodiment.

Here, the insulation material 12 which has been previously molded may be arranged to arrange the insulation material 12 in the space surrounded by the acoustic element 1, the partition part 10, and the case 9. Alternatively, as illustrated in FIG. 4, the insulation material 12 may be injected from a hole 13 by providing the hole 13, which is communicated with the space between the acoustic element 1 and the partition part 10, in one part of the case 9. That is, after the upper and lower parts of the case 9 has been engaged, the insulation material 12 is injected from the hole 13. After injecting the insulation material 12, the hole 13 is sealed with a lid 14 so as to cover the hole 13. According to this, the space surrounded by the acoustic element 1, the partition part 10, and the case 9 can be filled with the insulation material 12 surely without a gap. At this time, the hole 13 is sealed with the lid 14 in a state where the space on the side of the acoustic element 1 in the case 9 has been filled with the insulation material 12. That is, at least an opening on the side of the acoustic element 1 of the hole 13 is sealed with the insulation material 12. The lid 14 may be formed of the insulation material 12.

Figure 2:
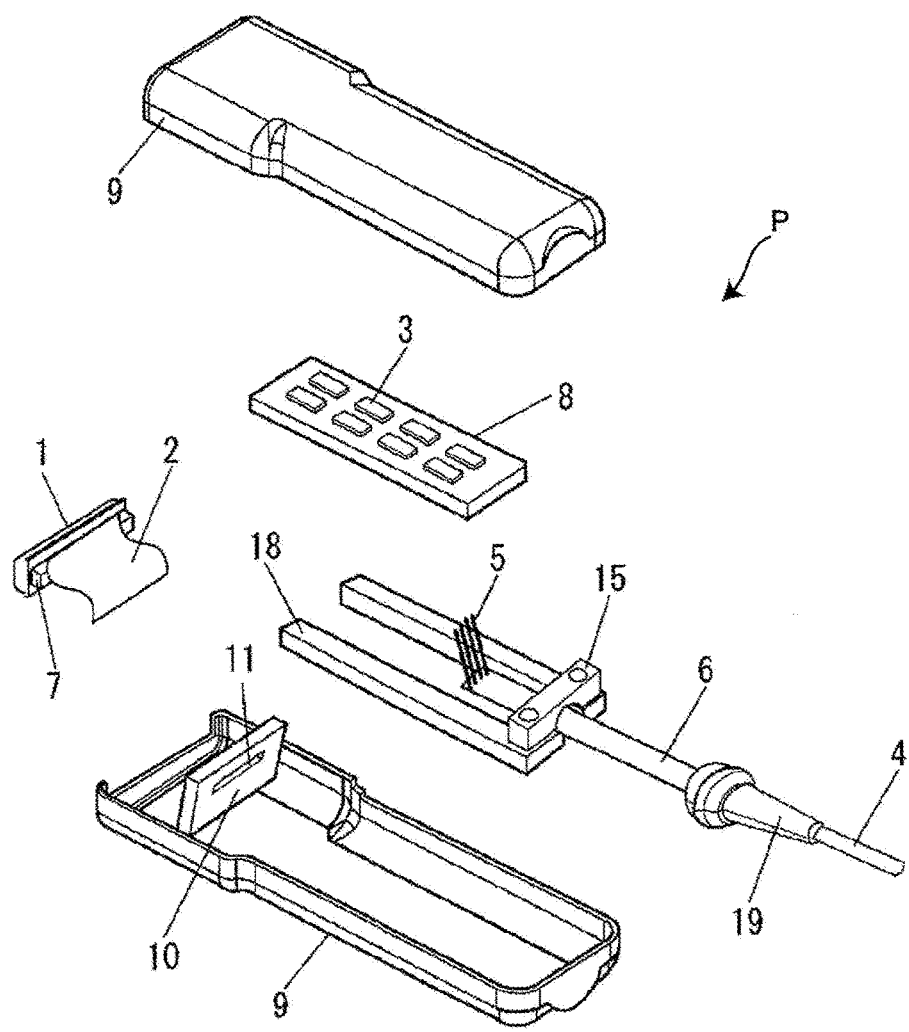
FIG. 2 is a three-dimensional figure of an example in which each component of the ultrasound probe P according to the first embodiment is disassembled.
Figure 3:
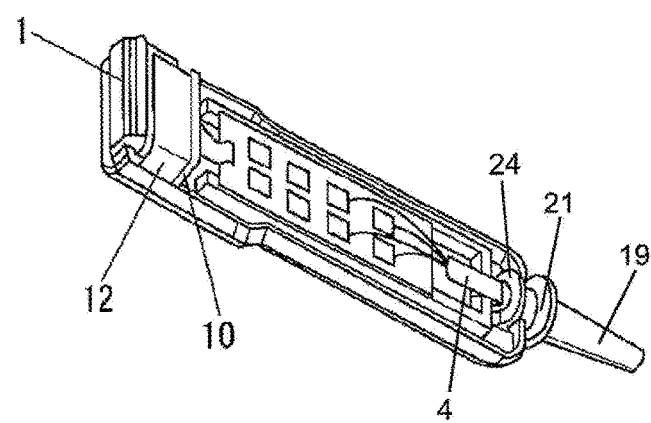
FIG. 3 is a view of an example in which a state where one side of a case of the ultrasound probe P according to the first embodiment is separated and each component is assembled can be seen.

FIG. 2 is a three-dimensional diagram in which each component of the ultrasound probe P according to the first embodiment is disassembled. FIG. 3 is a view of each component of the ultrasound probe P according to the first embodiment of the ultrasound probe P in a state where one side (upper side) of the case 9 is separated. The ultrasound probe P illustrated in FIGS. 2 and 3, after each component has been stored in the case 9 and the case 9 has been bonded, the insulation material 12 is injected into the hole 13 provided at the position corresponding to the space between the acoustic element 1 and the partition part 10 in the case 9 as illustrated in FIG. 4. After that, the hole 13 is sealed with the lid 14.

The space on the side of the electric signal processing circuit 3 in the case 9 separated by the partition part 10 is a space on the side of the electric signal processing circuit 3 surrounded by the partition part 10 and the case 9. The space is filled with gas such as air. That is, gas contacts with the electric signal processing circuit 3.

A cable clamp 15 is arranged in the case 9, and the cable shield 6 which is a part of the cable 4 is sandwiched by the cable clamp 15. The cable clamp 15 includes at least two parts, i.e., an upper and lower parts. The cable clamp 15 sandwiches the cable shield 6 in a state where fastening surfaces 16 of the two parts of the cable clamp 15 face to each other. In this state, a screw 17 passes through both parts of the cable clamp 15 so that the cable clamp 15 and the cable 4 are fixed. In FIGS. 1A and 1B, a case where a strain relief 19 has a T-shape in a plane view is illustrated. However, a case where the shape of the strain relief 15 is a rectangle in a plane view is illustrated in FIG. 2.

At least one or more arms 18 are connected to the cable clamp 15. The arm 18 is also connected to the circuit unit board 8. That is, the arm 18 supports the cable clamp 15 and the circuit unit board 8. In the first embodiment, the circuit unit board 8 and the arm 18 are fixed to each other with a screw 17. In the first embodiment, two arms 18 are connected to the cable clamp 15. However, the number of the arms 18 may be one and equal to or more than three. The arm 18 may be integrally formed with the cable clamp 15 as a part of the cable clamp 15. That is, the cable clamp 15 and the arm 18 may be formed of a single continuous member. For example, the cable clamp 15 and the arm 18 may be made by being integrally molded by using a metal die cast such as an aluminum die cast. Accordingly, a complicated shape suitable for fixing the cable 4 and dissipating the heat from the electric signal processing circuit 3 can be inexpensively realized. Also, when the arm 18 has been integrally formed with the cable clamp 15 as a part of the cable clamp 15, the cable clamp 15 sandwiches the cable shield 6 in the vertical direction with a part connected to the arm 18 (lower part) and a part opposite thereto (upper part) as illustrated in FIG. 1B. Accordingly, the heat of the circuit unit board 8 can be efficiently transferred to the cable shield 6 via the arm 18.

In addition, the structure is not limited to the case as the first embodiment in which the cable clamp 15 is pressure-welded by the screw 17 so that the cable clamp 15 sandwiches the cable shield 6. The cable shield 6 may be bonded to the arm 18 without providing the cable clamp 15. In this case, the bond may be performed by using an adhesive with high thermal conductivity or high conductivity. Also, it is not necessary to sandwich the cable shield 6 by the cable clamp 15. That is, the cable shield 6 may be bonded and fixed to a part of the cable clamp 15 by using the adhesive with high thermal conductivity or high conductivity without providing the screw 17 for performing the pressure-weld to the cable clamp 15.

The arm 18 is formed of a material having higher thermal conductivity than that of the insulation material 12. By employing such a material, the heat generated on the side of the electric signal processing circuit 3 can be transferred to the cable shield 6 via the arm 18 while preventing the heat transfer to the acoustic element 1.

For example, metal material such as gold, silver, and copper is preferable as the materials of the cable clamp 15 and the arm 18. In addition, cheap and lightweight aluminum which has low electric resistivity and high thermal conductivity is more preferable from among the metal materials. As employing these materials, a ground electrode of the electric signal processing circuit 3 may be arranged in the contact part of the circuit unit board 8 with the arm 18. With this arrangement, the cable 4 can be fixed by sandwiching the cable shield 6 by the cable clamp 15, and additionally, the ground electrode of the electric signal processing circuit 3 can be electrically connected to the cable shield 6 which is a comparatively thick wire. Accordingly, a ground impedance of the electric signal processing circuit 3 can be reduced. By reducing the ground impedance, the electric signal processing circuit 3 can reduce the effect of an electromagnetic wave noise from outside or reduce the electromagnetic wave noise to be released to outside.

Also, the heat generated by the electric signal processing circuit 3 is transferred to the cable shield 6 via a wide ground electrode formed on the circuit unit board 8 and the arm 18 directly contacted with the ground electrode. With this structure, the heat can be efficiently dissipated by transferring the heat of the electric signal processing circuit 3 to the cable shield 6 without providing a heat transfer plate for dissipating the heat, a heat spreader, or an electromagnetic shield member.

Also, when the arm 18 has been formed of the metal, an emissivity is significantly changed according to the condition of a surface of the arm 18. For example, in a case of aluminum, the emissivity of a non-oxide surface having a wavelength of about 1.6 μm is 0.09. Whereas, when aluminum on the surface is oxidized to be an oxide surface, the emissivity is 0.4 (four times or more). Also, other than the oxidation treatment on the surface, the emissivity can be similarly improved by coating the surface of the arm 18 with a heat radiating coating (heat dissipating coating). Also, the oxidation treatment may be performed on the surface of the cable clamp 15 connected to the arm 18 formed of aluminum. By oxidizing the surface of the cable clamp 15, the heat of the electric signal processing circuit 3 can be efficiently dissipated. The oxidation treatment may be performed to a whole surface of the arm 18 and the cable clamp 15. Alternatively, a part close to the cable 4 and where the cable clamp 15 is arranged in the arm 18 may be oxidized or coated with the heat dissipating coating. A structure may be used in which the surface on the side of the cable clamp 15 from the center in the longitudinal direction in the arm 18 is oxidized or coated with the heat dissipating coating, and the surface on an end of the opposite side of the cable clamp 15 from the center in the longitudinal direction of the arm 18 is not oxidized or coated with the heat dissipating coating. Accordingly, since the heat dissipation from near the cable 4 where the increase in the temperature is comparatively small can be increased, the increase in the temperatures in the acoustic element 1 and the case 9 can be further reduced. Alternatively, a part for contacting with the cable clamp 15 on the surface of the arm 18 may be oxidized or coated with the heat dissipating coating.

In addition, the cable clamp 15 and the arm 18 may be formed of a resin with which carbon or metal filler is compounded. In this case, a complicated form suitable for fixing the cable 4 and dissipating the heat from the electric signal processing circuit 3 can be inexpensively made by resin molding. Carbon black, carbon fiber, graphite, carbon graphite, or the like can be used as carbon. Fine powders such as silver, copper, nickel, and the like, metallic oxide such as zinc oxide or tin oxide, or metal fiber such as aluminum or stainless, and the like can be used as the metal filler. Polyolefin, polyester, phenol, or nylon can be used as the resin. The conductive resin with which such carbon or metal filler is compounded has a small electrical resistance and higher thermal conductivity than that of the general resin. Therefore, the above-mentioned conductive resin is suitable for dissipating the heat from the electric signal processing circuit 3 and reducing the ground impedance.

In addition, a part where the circuit unit board 8 contacts with the arm 18 may be coated with heat dissipating grease having higher thermal conductivity than that of the circuit unit board 8. According to this, a heat transfer efficiency from the electric signal processing circuit 3 to the arm 18 can be improved. For example, silicone grease having thermal conductivity of about 3 W/m·K can be used as the heat dissipating grease. Also, when the heat dissipating grease has not only the high thermal conductivity but also the conductivity, the ground impedance of the electric signal processing circuit 3 can be reduced. Therefore, an electromagnetic wave noise and radiation noise from outside can be reduced. In order to make the grease with high thermal conductivity to be conductive grease, it is preferable to mix carbon or metal filler. Fine powders such as silver, copper, or nickel, metallic oxide such as zinc oxide or tin oxide, metal fiber such as aluminum or stainless, and the like can be used as the metal filler. Carbon black, carbon fiber, graphite, carbon graphite, or the like can be used as carbon.

A strain relief 19 is provided in the place where the case 9 is connected to the cable 4, and the strain relief 19 allows the cable 4 to pass through the case 9. Specifically, the strain relief 19 is provided which allows the cable 4 to pass through the case 9 outside thereof and contacts with the case 9. The strain relief 19 is provided to prevent a disconnection of the cable 4 caused by a sharp curve.

The cable clamp 15 is connected to a heat dissipating plate in the case 24 to be described, and in addition, the heat dissipating plate in the case 24 is connected to a screw part 20 extending toward the outside of the case 9. The screw part 20 is screwed in a radiation plate 21 (second heat dissipating plate 21). The heat dissipating plate 21 is one or more circular plates which are insert molded in the strain relief 19 and formed of metal such as aluminum. A screw hole which is screwed to the screw part 20 is formed at the center of the heat dissipating plate 21. In the first embodiment, three circular heat dissipating plates 21 are included. With this structure, the screw part 20 is coupled with the heat dissipating plate 21 by rotating the heat dissipating plate 21 together with the strain relief 19 and being screwed in the screw part 20. A part coupled by the screw may be coated with high thermal conductive grease or high thermal conductive adhesive in order to improve the heat transfer efficiency. However, a method is not limited to the method using the screw, and the cable clamp 15 may be coupled with the heat dissipating plate 21 by using other method. Also, the cable clamp 15, the heat dissipating plate in the case 24, and the screw part 20 may be integrally formed. At this time, the part where the cable clamp 15, the heat dissipating plate in the case 24, and the screw part 20 are integrally formed includes two parts, i.e., an upper and lower parts, to sandwich the cable 4. The two parts are fixed with the screw 17. The integrally formed structure is preferable because a thermal conduction efficiency is higher than that of a structure in which the parts are connected with each other after being separately formed.

A cross-sectional area of the strain relief 19 covering the heat dissipating plate 21 gradually becomes smaller toward the side of the ultrasound diagnosis apparatus from a connection part (contact part) with the cable clamp 15 in the axis direction of the cable 4. The cable 4 can be prevented from being sharply bent by the shape of the strain relief 19. Accordingly, the disconnection of the signal line 5 of the cable 4 and the cable shield 6 can be prevented. In addition, for example, a surrounding area of the heat dissipating plate 21 produced of metal such as aluminum may be covered with the strain relief 19 formed of high thermal conductive and non-conductive elastomer. Accordingly, electrical insulation of the ultrasound probe P can be secured. At the same time, the emissivity of the elastomer is about 0.95 and is far higher than that of the metal such as aluminum. Therefore, more efficient heat dissipation can be realized by covering the heat dissipating plate 21 with the strain relief 19 formed of the elastomer.

The arm 18 and the cable clamp 15 may be produced as separate parts. However, the structure is not limited to this. For example, after the arm 18 and the cable clamp 15 have been produced as a single part according to machining, metal die cast, or resin molding, the arm 18 may be divided from the cable clamp 15. According to this method, the screw part 20 can be made before the arm 18 and the cable clamp 15 are divided.

Also, the cable 4 sandwiched by the cable clamp 15 can be firmly fixed by screwing the strain relief 19 in which the heat dissipating plate 21 is inserted in the screw part 20. A groove 23 may be formed in the screw part 20. The groove 23 extends in a direction perpendicular to the direction to which the cable 4 is sandwiched by the cable clamp 15 (axis direction of cable 4). The screw part 20 is divided into a plurality of regions (for example, three or four) by forming at least one groove 23. Accordingly, when the strain relief 19 is screwed in the screw part 20, the cable 4 can be fastened from a plurality of directions (for example, three or four). Therefore, the cable 4 can be more firmly fixed. Also, when a front end of the screw part 20 is thin and has a tapered shape, this is advantageous when the cable 4 is fastened by screwing the strain relief 19 in the screw part 20.

In addition, in a bonding part of the parts of the case 9, the heat dissipating plate in the case 24 (first heat dissipating plate 24) may be formed so as to be sandwiched by two parts of the case 9. The heat dissipating plate in the case 24 contacts with the cable clamp 15 and the heat dissipating plate 21. With this structure, the heat of the cable clamp 15 is transferred to the heat dissipating plate in the case 24. Therefore, heat dissipation can be improved. The heat dissipating plate in the case 24 is formed of the metal material such as aluminum. In addition, as illustrated in FIGS. 1A and 1B, the heat dissipating plate in the case 24 and the heat dissipating plate 21 may be arranged so as to contact with each other. By the heat dissipating plate in the case 24 and the heat dissipating plate 21, the cable 4 is surrounded and the heat dissipating plate to be connected to the cable clamp 15 is formed. Accordingly, the more heat of the cable clamp 15 can be transferred to the heat dissipating plate 21 via the heat dissipating plate in the case 24. Therefore, compared with a case where the heat dissipating plate in the case 24 is not included, the heat transfer efficiency of the heat generated by the electric signal processing circuit 3 to the heat dissipating plate 21 can be increased. As a result, a heat dissipation efficiency to the outside via the heat dissipating plate 21 on the side of the strain relief 19 can be improved.

Also, hollows 22 may be formed in connecting parts of the case 9 and the strain relief 19. In FIGS. 1A and 1B, the hollow 22 formed in the case 9 faces to the hollow 22 formed in the strain relief 19. When the adhesive is applied between the case 9 and the strain relief 19 and both the case 9 and the strain relief 19 are bonded to each other, the hollow 22 functions as a space to store the adhesive. Accordingly, the excessive adhesive is stored in the hollow 22. When water is entered from a gap between the strain relief 19 and the case 9, the adhesive is stored in the hollow 22 and cured so that an inflow path of the water until the water reaches the inside of the case 9 becomes longer than that of a case where the hollows 22 are not provided. Accordingly, since the inflow of the water from outside can be more surely prevented, the electrical insulation properties can be more certainly secured.

Also, a contact surface of the cable clamp 15 with the cable shield 6 may be uneven. By providing this uneven surface, the cable 4 can more firmly fixed. At the same time, since a heat transfer area from the cable clamp 15 to the cable shield 6 becomes wider, heat transfer effect to dissipate the heat can be more improved.

In addition, the contact surface of the cable clamp 15 with the cable 4 may be coated with the grease or adhesive with higher thermal conductivity than that of the cable clamp 15. By being coated with the grease or adhesive, the heat transfer efficiency from the cable clamp 15 to the cable shield 6 is improved. When the adhesive is used, the cable 4 is more surely fixed. For example, silicone grease with thermal conductivity of about 3 W/m·K can be used as the grease with high thermal conductivity. Also, it is preferable that the grease or adhesive have conductivity. A ground of the electric signal processing circuit 3 can be electrically connected to the cable 4 with a low impedance by coating the conductive grease or adhesive on the cable clamp 15. Accordingly, an effect of the electromagnetic wave noise from outside and the electromagnetic wave noise to be released to outside can be reduced. To make the grease or adhesive with high thermal conductivity become conductive, it is preferable to mix carbon or metal filler. For example, fine powders such as silver, copper, and nickel, metallic oxide such as zinc oxide or tin oxide, and metal fiber such as aluminum or stainless can be used as metal filler. For example, carbon black, carbon fiber, graphite, and carbon graphite can be used as carbon.

Here, to describe the effects of the present disclosed technique, a simulation result of a heat generation state of the ultrasound probe will be described with reference to FIGS. 5 to 11.

Figure 5:
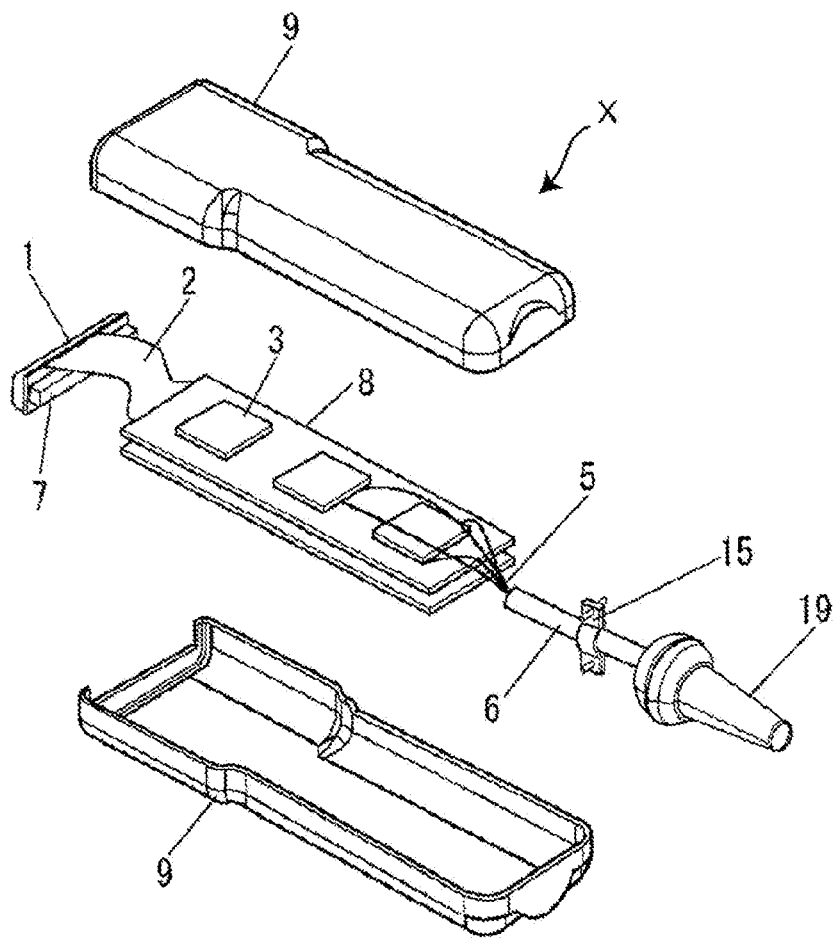
FIG. 5 is an explanatory diagram of the ultrasound probe used to simulate transfer of the heat generated from an electric signal processing circuit.

FIG. 5 is an exploded view of an ultrasound probe X used for the simulation. The ultrasound probe X includes an acoustic element 1, an acoustic element board 2, an electric signal processing circuit 3, a signal line 5, a cable shield 6, a backing material 7, a circuit unit board 8, a case 9, a cable clamp 15, and a strain relief 19. At the point where these components are included, the ultrasound probe X illustrated in FIG. 5 is common with the ultrasound probe P illustrated in FIGS. 1A to 3. The structures of the electric signal processing circuits 3 and the shapes of the cable clamps 15 in the ultrasound probes P and X are different from each other. However, the basic structures are generally similar to each other, and the symbols used in FIGS. 1A to 3 are used in the ultrasound probe X illustrated in FIG. 5. To simplify the structure, the electromagnetic shield member is omitted. The acoustic element 1 is electrically connected to the electric signal processing circuit 3 via the acoustic element board 2. The electric signal processing circuit 3 is electrically connected to an ultrasound diagnosis apparatus via the signal line 5. A state before the two parts of the case 9 are bonded is illustrated in FIG. 5. However, at the time of the simulation, the two parts of the case 9 are bonded so as to include the acoustic element 1, the electric signal processing circuit 3, the cable shield 6, the cable clamp 15, and the like.

First, a simulation result of an ultrasound probe X1 in which a partition part for dividing a space in the case 9 in the ultrasound probe X has not been provided will be described with reference to FIGS. 6A to 7B.

Figure 6A:
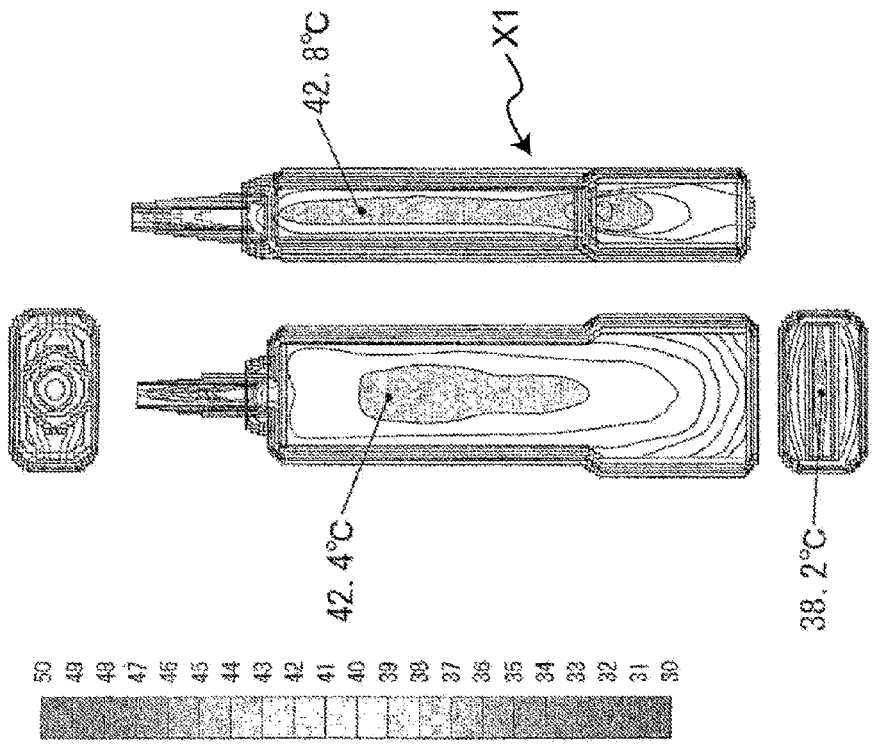
FIG. 6A is a diagram of a calculation result of a surface temperature on the ultrasound probe in a case where the acoustic element of the ultrasound probe is held upward relative to the ground.
Figure 6B:
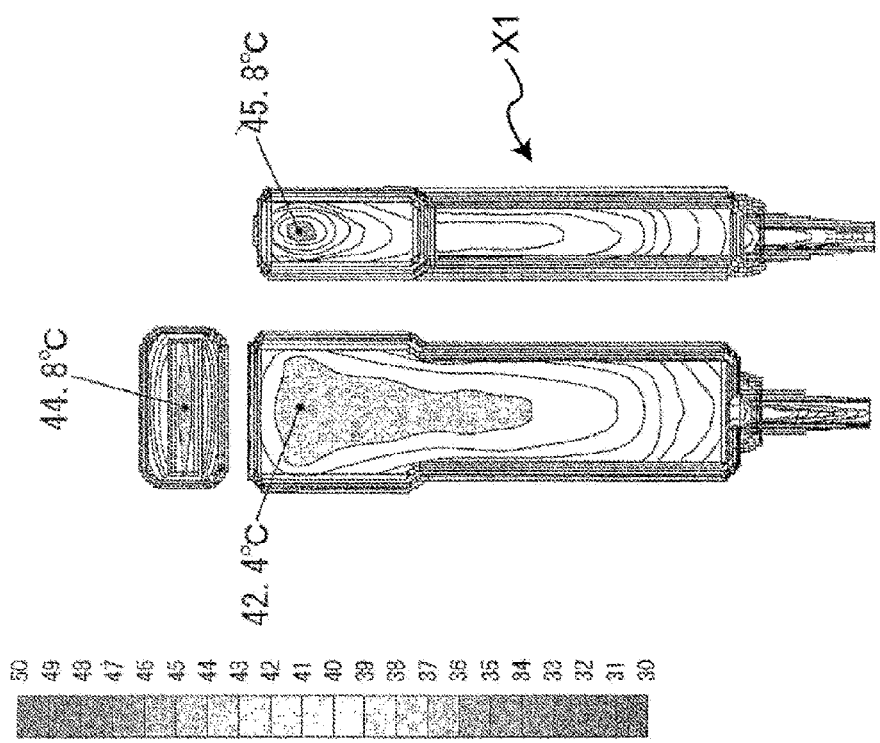
FIG. 6B is a diagram of a calculation result of a surface temperature on the ultrasound probe in a case where the acoustic element of the ultrasound probe is held downward relative to the ground.

In FIGS. 6A and 6B, a simulation result is illustrated in which a surface temperature of each part in a case where the power is not applied to the acoustic element 1 and the power consumption of the electric signal processing circuit 3 is assumed to be 3 W is calculated by using the ultrasound probe X1. The simulation result in a case where the whole case 9 is filled with air is illustrated in FIGS. 6A and 6B. FIG. 6A indicates a simulation result in a case where the acoustic element 1 of the ultrasound probe X1 is held upward relative to the ground. FIG. 6B indicates a simulation result in a case where the acoustic element 1 of the ultrasound probe X1 is held downward relative to the ground.

As illustrated in FIG. 6A, when the acoustic element 1 of the ultrasound probe X1 is held upward, the temperature of the acoustic element 1 is increased up to 44.8° C. by propagation of heat of the electric signal processing circuit 3. In addition, the temperature of the side surface of the case 9 is increased up to 45.8° C. by the convection of the air in the case 9. On the other hand, as illustrated in FIG. 6B, when the acoustic element 1 of the ultrasound probe X1 is held downward, the temperature of the acoustic element 1 is about 38.2° C. However, the temperature of the side surface of the case 9 is increased up to 42.8° C. by the convection of the air in the case 9.

When being used, the ultrasound probe X1 is faced to any directions. On the other hand, when the ultrasound probe X1 is not used, the ultrasound probe X1 is stored in a probe holder (not shown) of the ultrasound diagnosis apparatus, for example, in a state where the acoustic element 1 faces upward. In this situation, since the heat generated by the electric signal processing circuit 3 is transferred to the acoustic element 1 by the convection of the air in the case 9, the temperature of the acoustic element 1 is increased. Since the acoustic element 1 has a limit temperature, a voltage which can be applied to the acoustic element 1 is limited when the temperature of the acoustic element 1 increases. According to this, a problem occurs in that the output of transmission voltage to the ultrasound probe X1 cannot be increased up to a necessary ultrasound output value and the sensitivity of the ultrasound diagnosis apparatus decreases. According to this simulation result, the inventors have found that especially in a case where the acoustic element 1 is held upward, the propagation of heat by the convection of the air in the case 9 causes a serious increase in the temperature of the acoustic element 1.

Next, a heat generation state of an ultrasound probe X2 will be described in which the partition part for dividing the space in the case 9 of the ultrasound probe X is not provided and the whole case 9 is filled with the insulation material other than air.

FIGS. 7A and 7B indicate simulation results in which the surface temperature of each part of a following case is calculated by using the respective ultrasound probes X1 and X2. The above case is when the power is not applied to the acoustic element 1 and the power consumption of the electric signal processing circuit 3 is assumed to be 3 W in a state where the acoustic element 1 is held upward. FIG. 7A indicates the simulation result (result indicated in FIG. 6A) in a case where the whole space in the case 9 is filled with air as a comparison object. FIG. 7B indicates the simulation result in a case where the whole space in the case 9 is filled with the insulation material other than air, specifically, rigid urethane foam.

As illustrated in FIG. 7A, when the whole space in the case 9 is filled with air, the maximum surface temperature of the acoustic element 1 is 44.8° C., the maximum surface temperature of a front surface of the case 9 (a surface on the side where the electric signal processing circuit 3 is arranged) is 42.4° C., and the maximum surface temperature of the side surface of the case 9 is 45.8° C. As illustrated in FIG. 7B, when the whole space in the case 9 is filled with the insulation material other than air, the maximum surface temperature of the acoustic element 1 is 50.9° C., the maximum surface temperature of the front surface of the case 9 is 45.2° C., and the maximum surface temperature of the side surface of the case 9 is 49.3° C. According to these results, it is found that the surface temperatures of the acoustic element 1 and the case 9 in a case where the whole space in the case 9 is filled with the insulation material other than air are higher than those in a case where the whole space in the case 9 is filled with air. According to this, it is found that there is no effect to reduce the surface temperatures of the acoustic element 1 of the electric signal processing circuit 3 and the case 9 and the surface temperature of a specific part increases even when the whole space in the case 9 is filled with the insulation material other than air.

Next, a heat generation state of an ultrasound probe X3 in which the partition part 10 for dividing the space in the case 9 is provided in the ultrasound probe X will be described with reference to FIG. 8. The partition part 10 for spatially separating the acoustic element 1 and the electric signal processing circuit 3 and arranged so as to contact with the case 9 is provided between the acoustic element 1 and the electric signal processing circuit 3 in the ultrasound probe X3. Also, in the separated space in the case 9, the space on the side of the acoustic element 1 is filled with the insulation material other than air, specifically, the rigid urethane foam, and the space on the side of the electric signal processing circuit 3 is filled with air.

Figure 8:
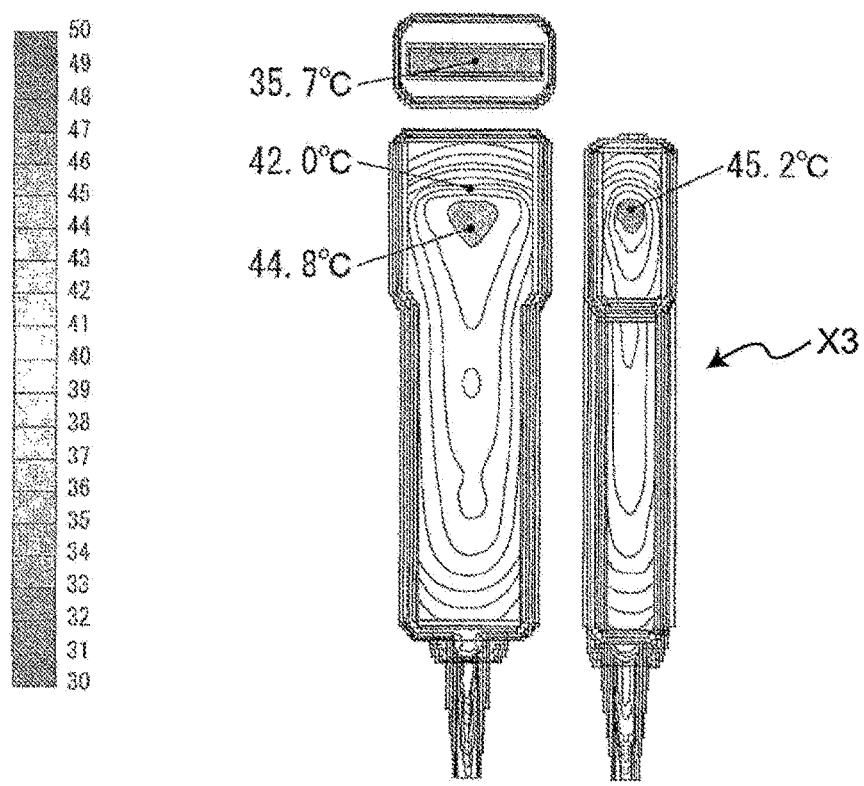
FIG. 8 is a diagram of a calculation result of a surface temperature on the ultrasound probe in a case where a space between the acoustic element and a partition part in the case is filled with the insulation material and the air exists in a space between the electric signal processing circuit and the case.

FIG. 8 indicates a simulation result in which the surface temperature of each part in the ultrasound probe X3 is calculated in a following case. The above case is when the power is not applied to the acoustic element 1 and the power consumption of the electric signal processing circuit 3 is assumed to be 3 W in a state where the acoustic element 1 is held upward relative to the ground. As illustrated in FIG. 8, the maximum surface temperature of the acoustic element 1 is 35.7° C. This is lower than the temperature (44.8° C.) in a case where the whole space in the case 9 is filled with air described with reference to FIG. 7A. As illustrated in FIG. 8, the maximum surface temperature of the front surface of the case 9 is 44.8° C., and the maximum surface temperature of the side surface of the case 9 is 45.2° C.

In addition, a heat generation state of an ultrasound probe X4 in a case where the circuit unit board 8 is connected to the arm 18 in the ultrasound probe X3 used in FIG. 8 will be described with reference to FIG. 9. The ultrasound probe X4 in which the cable clamp 15 and the circuit unit board 8 are connected to the arm 18 is used in FIG. 9.

Figure 9:
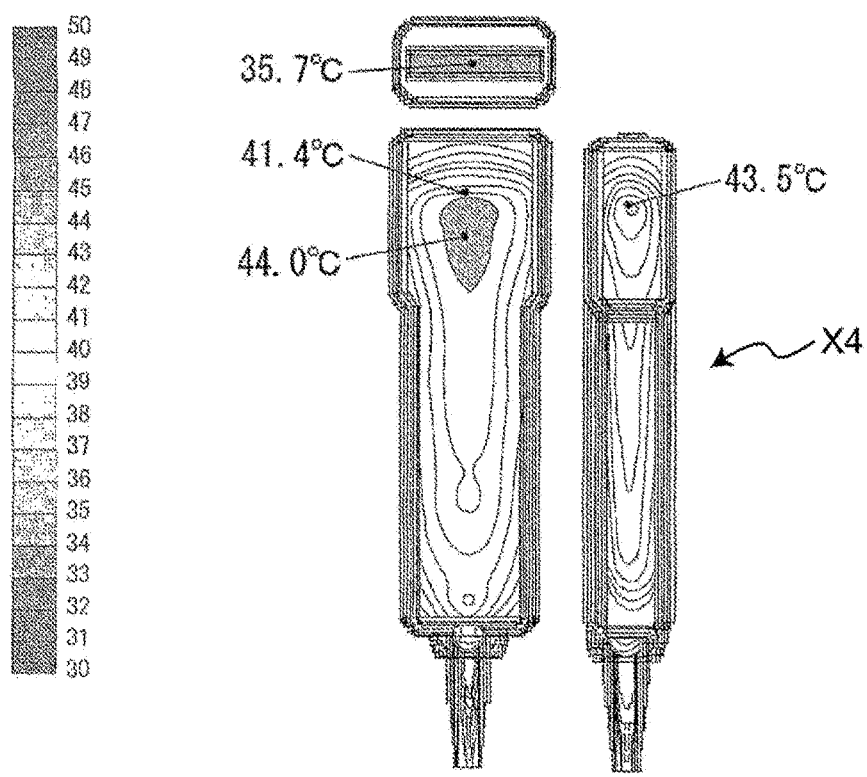
FIG. 9 is a diagram of a calculation result of a surface temperature on the ultrasound probe in a case where the space between the acoustic element and the partition part in the case is filled with the insulation material and a circuit unit board is connected to an arm.

FIG. 9 indicates a simulation result in which the surface temperature of each part in the ultrasound probe X4 is calculated in a following case. The above case in when the power is not applied to the acoustic element 1 and the power consumption of the electric signal processing circuit 3 is assumed to be 3 W in a state where the acoustic element 1 is held upward relative to the ground. As illustrated in FIG. 9, the maximum surface temperature of the acoustic element 1 is 35.7° C., the maximum surface temperature of the front surface of the case 9 is 44.0° C., and the maximum surface temperature of the side surface of the case 9 is 43.5° C. The maximum surface temperature of the acoustic element 1 in FIG. 9 (35.7° C.) is lower than the temperature of a case described with reference to FIG. 7A (44.8° C.). In addition, it is found that the maximum surface temperature of the front surface of the case 9 in FIG. 9 (44.0° C.) is lower than the temperature in a case where the arm 18 is not provided described with reference to FIG. 8 (44.8° C.). In the ultrasound probe X4 illustrated in FIG. 9, the heat generated from the electric signal processing circuit 3 can be efficiently transferred to the strain relief 19 via the arm 18 and the cable clamp 15 by connecting the circuit unit board 8 to the arm 18. Accordingly, not only the surface temperature of the acoustic element 1 but also the surface temperature of the front surface of the case 9 can be reduced.

Next, a heat generation state of an ultrasound probe X5 in a case where non-conductive high thermal conductive PBT is used as a material of the case 9 in the ultrasound probe X1 used in FIGS. 6A and 6B will be described with reference to FIGS. 10A and 10B.

Figure 10B:
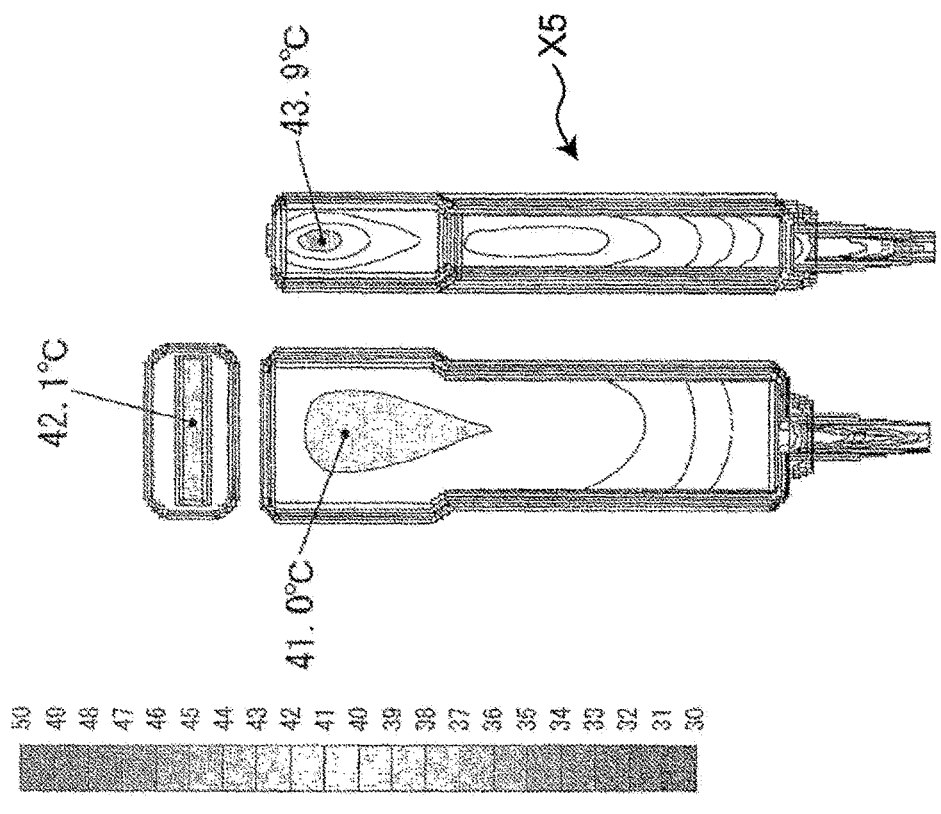
FIG. 10B is a diagram a calculation result of a surface temperature on the ultrasound probe in a case where nonconductive high heat conductive PBT is used as the material of the case.
Figure 10A:
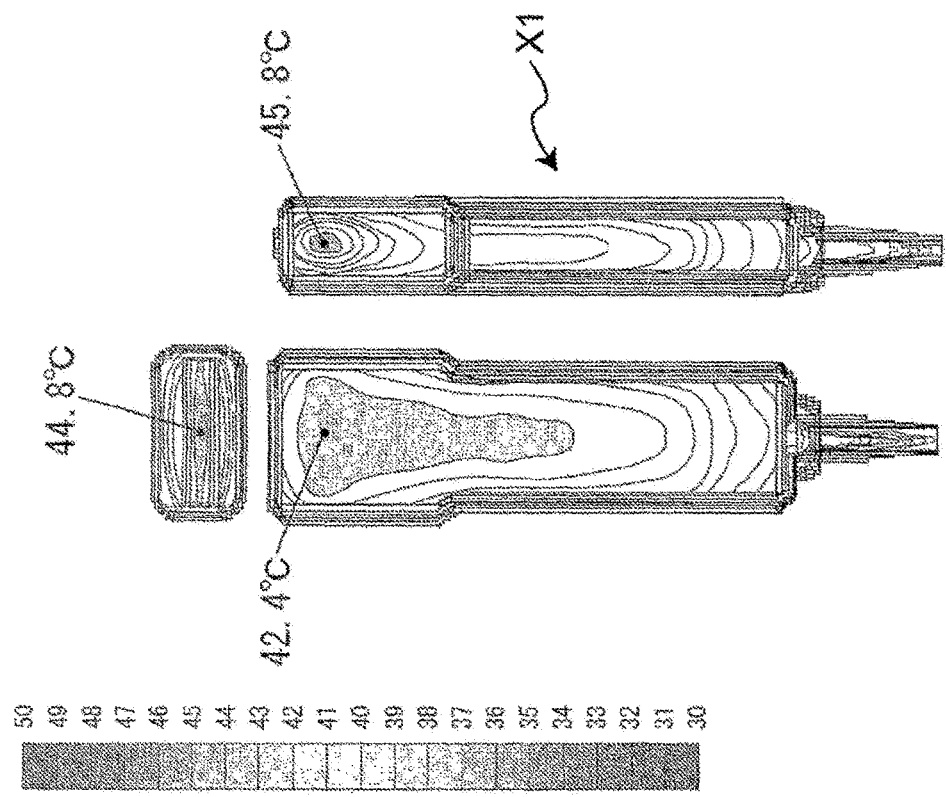
FIG. 10A is a diagram of a calculation result of a surface temperature on the ultrasound probe in a case where a modified PPE resin is used as a material of the case.

FIGS. 10A and 10B indicate simulation results in which the surface temperature of each part in the respective ultrasound probes X1 and X5 are calculated in a following case. The above case is when the power is not applied to the acoustic element 1 and the power consumption of the electric signal processing circuit 3 is assumed to be 3 W in a state where the acoustic element 1 is held upward relative to the ground. FIG. 10A is a simulation result (result indicated in FIG. 6A) in a case where a modified PPE resin is used as the material of the case 9 as the comparison object. FIG. 10B is a simulation result in a case where non-conductive high thermal conductive PBT in which filler of boron nitride is mixed with a PBT resin is used as the material of the case 9. As illustrated in FIG. 10A, when a modified PPE resin is used as the material of the case 9, the maximum surface temperature of the acoustic element 1 is 44.8° C., the maximum surface temperature of the front surface of the case 9 is 42.4° C., and the maximum surface temperature of the side surface of the case 9 is 45.8° C. On the other hand, as illustrated in FIG. 10B, when a non-conductive high thermal conductive PBT is used as the material of the case 9, the maximum surface temperature of the acoustic element 1 is 42.1° C., the maximum surface temperature of the front surface of the case 9 is 41.0° C., and the maximum surface temperature of the side surface of the case 9 is 43.9° C. According to these results, as illustrated in FIG. 10B, it is found that the heat transferred from the acoustic element 1 and the electric signal processing circuit 3 to the case 9 is efficiently diffused by using the resin with high thermal conductivity as the material of the case 9 so that the surface temperatures of the acoustic element 1 and the case 9 are reduced.

Figure 11:
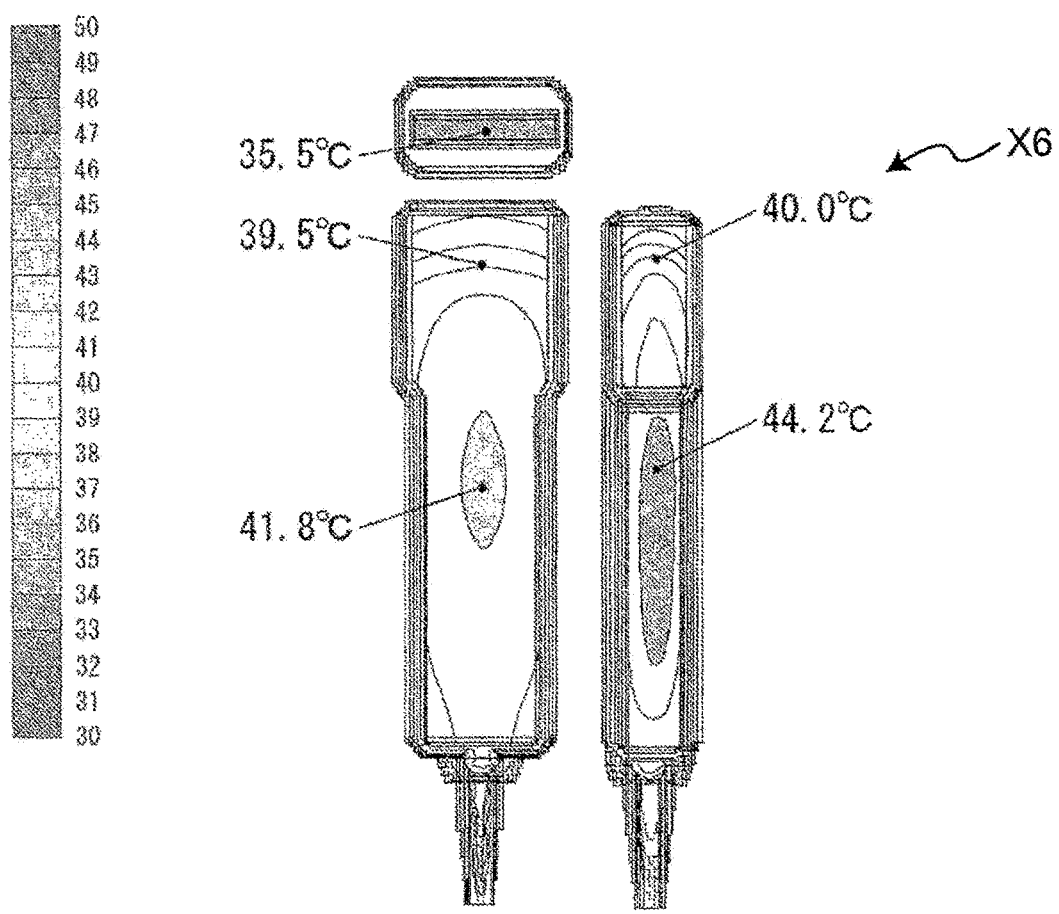
FIG. 11 is a diagram a calculation result of a surface temperature on the ultrasound probe in a case where the space between the acoustic element and the partition part in the case is filled with the insulation material, and the circuit unit board is connected to the arm, and the nonconductive high heat conductive PBT is used as the material of the case.

In the ultrasound probe X4 illustrated in FIG. 9, a heat generation state of an ultrasound probe X6 using a high thermal mission conductive PBT as a material of the case 9 will be described with reference to FIG. 11. FIG. 11 indicates a simulation result in which the surface temperature of each part in the ultrasound probe X6 is calculated in a following case. The above case is when the power is not applied to the acoustic element 1 and the power consumption of the electric signal processing circuit 3 is assumed to be 3 W in a state where the acoustic element 1 is held upward relative to the ground. As illustrated in FIG. 11, the maximum surface temperature of the acoustic element 1 is 35.5° C., the maximum surface temperature of the front surface of the case 9 is 41.8° C., and the maximum surface temperature of the side surface of the case 9 is 44.2° C. Therefore, compared with the case of the ultrasound probe X1 illustrated in FIGS. 6A and 6B, the surface temperatures of the acoustic element 1 and the case 9 can be reduced even when the acoustic element 1 is held upward relative to the ground.

As described above, in the ultrasound probes X3, X4, and X6 (FIGS. 8, 9, and 11) according to the first embodiment of the present disclosed technique, the partition part 10 formed so as to contact with the insulation material 12 and the case 9 separates the space in the case 9 into the space on the side of the acoustic element 1 and the space on the side of the electric signal processing circuit 3. According to this, the convection of the air between the space on the side of the acoustic element 1 and the space on the side of the electric signal processing circuit 3 in the case 9 is eliminated, and the transfer of the heat from the electric signal processing circuit 3 to the acoustic element 1 can be prevented. That is, a thermal insulation layer (insulation material 12) is formed between the partition part 10 and the acoustic element 1 in the case 9. Alternatively, it can be said that thermal insulation medium (insulation material 12) is filled. Also, as described with reference to FIG. 9 and the like, the heat generated by the electric signal processing circuit 3 is efficiently transferred to the cable 4 and the strain relief 19 via the arm 18 for supporting the cable clamp 15. In addition, the heat generated by the electric signal processing circuit 3 is transferred to a part for covering the electric signal processing circuit 3 in the case 9 by the convection of the air in the space on the side of the electric signal processing circuit 3 in the case 9. Accordingly, the heat of the electric signal processing circuit 3 can be dissipated.

That is, each of the ultrasound probes X3, X4, and X6 (and ultrasound probe P) which can be connected to the ultrasound diagnosis apparatus includes the acoustic element 1 for converting the electric signal and the ultrasound to each other, the electric signal processing circuit 3 electrically connected to the acoustic element 1, the case 9 for storing the acoustic element 1 and the electric signal processing circuit 3, the acoustic element board 2 for electrically connecting the acoustic element 1 to the electric signal processing circuit 3, and the partition part 10 which is arranged so as to contact with the case 9 and separates the acoustic element 1 and the electric signal processing circuit 3. The space on the side of the acoustic element 1 separated by the partition part 10 in the case 9 is filled with the first material (insulation material 12) having lower thermal conductivity than that of a material which forms an inner wall surface of the case 9. Accordingly, the heat generated from the electric signal processing circuit 3 which is a heat source can be efficiently dissipated, and the heat transfer to the acoustic element 1 can be prevented. When at least having these components, the above-mentioned purpose of the present disclosed technique can be achieved.

In the first embodiment, especially in a state where the acoustic element 1 is held upward, the transfer of the heat generated by the electric signal processing circuit 3 and the like to the acoustic element 1 by the convection of the air can be prevented. Accordingly, the increase in the temperature of the acoustic element 1 can be reduced. Therefore, the sensitivity reduction of the ultrasound probe caused by the limitation of the ultrasound output related to the limitation of the surface temperature of the acoustic element 1 can be reduced.

First Modification of First Embodiment

FIG. 12A is a cross-sectional diagram of an ultrasound probe Q according to a first modification of the first embodiment. FIG. 12B is a cross-sectional diagram of the ultrasound probe Q in FIG. 12A viewed from an A-A' cross section. Here, the components of the ultrasound probe similar to those described in the first embodiment have the same symbols as those of the first embodiment, and the detailed description regarding the above components will be omitted.

In the first modification of the first embodiment, a partition plate 25 including a plurality of plates arranged at a predetermined interval and arranged so as to contact with the case 9 is formed as the partition part 10. A space between the plurality of partition plates 25 and a space between the partition plate 25 and the acoustic element 1 are filled with air.

More specifically, a continuous partition part including the plurality of partition plates 25 for spatially separating the acoustic element 1 and the electric signal processing circuit 3 is provided in one of the parts of the case 9 which is divided into two parts, i.e., upper and lower parts. Here, the partition plates 25 are integrally formed with the one part of the case 9. However, after being individually formed, the partition plates 25 may be arranged in the case 9. The outer surface of the case 9 is not separated by the partition plates 25 and covers from the acoustic element 1 to the electric signal processing circuit 3. The partition plates 25 are arranged so as to contact with the case 9, and the acoustic element board 2 passes through the partition plates 25. The acoustic element board 2 passes through the through-holes 11 provided in the respective partition plates 25. It is preferable that the size of the through-hole 11 be a size in which the partition plate 25 contacts with the acoustic element board 2. Also, it is possible that the partition plates 25 are not formed in one part of the case 9 and provided on the both sides of the two parts (upper and lower parts) of the case 9. In this case, the through-hole 11 through which the acoustic element board 2 passes may be formed by providing notches in the respective upper and lower partition plates 25. Also, the partition plate 25 may be formed of the similar material to that of the case 9 and integrally formed with the case 9. The partition plate 25 and the case 9 are bonded without a gap by integrally forming the partition plate 25 with the case 9. Accordingly, the convection of the air between the space on the side of the acoustic element 1 and the space on the side of the electric signal processing circuit 3 in the case 9 can be prevented.

Although four partition plates 25 are formed in FIGS. 12A and 12B, it is preferable to include at least two or more partition plates 25.

In this way, the transfer of the heat from the electric signal processing circuit 3 to the acoustic element 1 can be prevented by dividing the space in the case 9 by the partition plates 25 and providing an air layer in each divided space even when the insulation material other than air is not arranged in the case 9.

Second Modification of First Embodiment

FIG. 13A is a cross-sectional diagram of an ultrasound probe R according to a second modification of the first embodiment. FIG. 13B is a cross-sectional diagram of the ultrasound probe R in FIG. 13A viewed from an A-A' cross section. Here, the components of the ultrasound probe similar to those described in the first embodiment have the same symbols as those in the first embodiment, and the detailed description of those will be omitted.

In the second modification of the first embodiment, a partition plate 26 including two plates arranged at a predetermined interval and arranged so as to contact with the case 9 is used as the partition part 10. In addition, a space between the two partition plates 26 is filled with an insulation material 27 other than air so as to contact with a surface to which the partition plate 26 faces and the case 9. Also, a space between the acoustic element 1 and the partition plate 26 is filled with a high thermal conductive material 28 having higher thermal conductivity than that of the insulation material 27. That is, in the space on the side of the acoustic element 1 in the case 9 divided by the partition plate 26 is filled with the insulation material 27 and the high thermal conductive material 28.

More particularly, the two partition plates 26 for spatially separating the acoustic element 1 and the electric signal processing circuit 3 are provided in one part of the case 9 which is divided into two parts, i.e., the upper and lower parts. Here, the partition plates 26 are integrally formed with one part of the case 9. However, after being individually formed, the partition plates 26 may be arranged in the case 9. The outer surface of the case 9 is not separated by the partition plate 26 and covers from the acoustic element 1 to the electric signal processing circuit 3. The partition plates 26 are arranged so as to contact with the case 9, and the acoustic element board 2 passes through the partition plates 26. The acoustic element board 2 passes through the respective through-holes 11 provided in the partition plates 26. It is preferable that the size of the through-hole 11 be a size in which the partition plate 26 contacts with the acoustic element board 2. Also, it is possible that the partition plate 26 is not formed in one part of the case 9 and provided on both sides of the two parts (upper and lower parts) of the case 9. In this case, the through-hole 11 through which the acoustic element board 2 passes may be formed by providing the notches in the upper and lower partition plates 26. The partition plates 26 may be formed of the similar material as that of the case 9 and integrally formed with the case 9. The partition plates 26 and the case 9 are bonded without a gap by integrally forming the partition plates 26 with the case 9. Accordingly, the convection of the air between the space on the side of the acoustic element 1 and the space on the side of the electric signal processing circuit 3 in the case 9 can be prevented.

The insulation material 27 may be, for example, rigid urethane foam, expanded polystyrene foam, glass wool, rock wool, air, and wood. The high thermal conductive material 28 may be, for example, a mixture of a resin such as a PBT resin, a PPS resin, a nylon resin, and a phenol resin into the filler such as silicon carbide, aluminum nitride, boron nitride, magnesium oxide, aluminum oxide, and aluminum nitride.

When the insulation material 27 and the high thermal conductive material 28 are filled, each component of the ultrasound probe R is stored in the case 9, and the case 9 is bonded. After that, the case 9 may be sealed with a lid after the materials of the insulation material 27 and the high thermal conductive material 28 are injected from a hole provided in the case 9. The hole in the case 9 is communicated to the space in the case 9 where the insulation material 27 and the high thermal conductive material 28 are arranged. The insulation material 27 and the high thermal conductive material 28 can be filled in the case 9 surely without a gap by forming the hole in the case 9 and injecting the materials of the insulation material 27 and the high thermal conductive material 28 from the hole.

In the second modification of the first embodiment, the insulation material 27 is arranged between the partition plates 26, and the high thermal conductive material 28 is arranged between the acoustic element 1 and the partition plate 26. With this arrangement, the transfer of the heat generated by the electric signal processing circuit 3 to the acoustic element 1 can be prevented by the insulation material 27. Also, the heat generated in the acoustic element 1 can be dissipated by being transferred to the case 9 via the high thermal conductive material 28. Accordingly, the increase in the surface temperature of the acoustic element 1 can be reduced. Therefore, the sensitivity reduction of the ultrasound probe R caused by the limitation of the ultrasound output related to the limitation of the surface temperature of the acoustic element 1 can be reduced.

Second Embodiment

FIG. 14A is a cross-sectional diagram of an ultrasound probe S according to a second embodiment of the present disclosed technique. FIG. 14B is a cross-sectional diagram of an ultrasound probe S in FIG. 14A viewed from an A-A' cross section. Here, the components of the ultrasound probe similar to those described in the first embodiment have the same symbols as those of the first embodiment, and the detailed description regarding the above components will be omitted. One end of the ultrasound probe S can be connected to an ultrasound diagnosis apparatus (not shown) via a cable 4.

A difference between the first and second embodiments is a structure of a case 9. Specifically, the case 9 is divided into two parts, i.e., upper and lower parts, in the first embodiment. On the other hand, the case 9 is divided into an acoustic element case 29 (first part 29) for storing an acoustic element 1 and a circuit unit case 30 (second part 30) for storing an electric signal processing circuit 3 in the second embodiment.

The components such as the acoustic element 1, an acoustic element board 2, and the electric signal processing circuit 3 are stored in the case 9 by bonding the acoustic element case 29 for covering the acoustic element 1 to the circuit unit case 30 for covering the electric signal processing circuit 3 with an adhesive and the like. In this way, the acoustic element 1 and the electric signal processing circuit 3 are stored in the case 9.

It is preferable that the case 9 be formed of a material having insulation properties and high thermal conductivity (thermal conductive material with high insulation properties). The material may be, for example, mixture of a resin such as a PBT resin, a PPS resin, a nylon resin, and a phenol resin into a filler such as silicon carbide, aluminum nitride, boron nitride, magnesium oxide, aluminum oxide, and aluminum nitride. These materials have high thermal conductivity of 2 to 15 W/m·K and the insulation properties. The heat can be dispersed to the whole case 9 by using the high thermal conductive material as the material of the case 9. Therefore, the increase in the temperature of a specific part of the case 9 can be prevented. Also, when at least an inner surface of the case 9 (side where the acoustic element 1 and the like are stored) has the high thermal conductivity, the increase in the temperature of a specific part of the case 9 can be prevented regardless of the degree of the thermal conductivity of the outside of the case 9. Therefore, a layer of a material with high thermal conductivity may be formed on the inner surface of the case 9. For example, the inner surface of the case 9 may be coated with graphite as the material having high thermal conductivity. Specifically, the structure of the case 9 may be a structure in which a layer of the material with high thermal conductivity is formed on the inner surface of the circuit unit case 30 and a layer of the material with high thermal conductivity is not formed on the inner surface of the acoustic element case 29. This structure is preferable because the heat to be dissipated from the electric signal processing circuit 3 is dispersed and the heat dispersion to the side of the acoustic element 1 can be prevented.

An element case lid 31 for spatially separating the acoustic element 1 and the electric signal processing circuit 3 is provided between the acoustic element 1 and the electric signal processing circuit 3 in the case 9. The element case lid 31 corresponds to the partition part 10 in the first embodiment. The element case lid 31 is arranged so as to contact with the case 9, and the acoustic element board 2 passes through the element case lid 31. The acoustic element board 2 passes through the through-hole 11 provided in the element case lid 31. It is preferable that the size of the through-hole 11 be a size where the element case lid 31 contacts with the acoustic element board 2. The element case lid 31 covers an opening of the acoustic element case 29 (opening on the side of the electric signal processing circuit 3 of the acoustic element case 29). In addition, the element case lid 31 is formed on a plane including a bonding surface of the acoustic element case 29 and the circuit unit case 30. That is, the acoustic element case 29 and the circuit unit case 30 are bonded to each other at a position where they contact with the element case lid 31. The element case lid 31 may be formed of, for example, a modified PPE resin. Also, the element case lid 31 may be formed of a similar material to that of the case 9.

The space on the side of the acoustic element 1 separated by the element case lid 31 is filled with rigid urethane foam and the like as the insulation material 12 (first material 12) with low thermal conductivity. The space on the side of the acoustic element 1 separated by the element case lid 31 indicates a space surrounded by the acoustic element 1, the element case lid 31, and the acoustic element case 29 in the case 9, and specifically, indicates a space in the case 9 surrounded by the backing material 7 of the acoustic element 1, the element case lid 31, and the acoustic element case 29. It is preferable that the thermal conductivity of the insulation material 12 be lower than that of at least the inner surface of the acoustic element case 29. Therefore, the insulation material 12 may be air. However, it is preferable that the insulation material 12 be a solid material. In addition, for example, expanded polystyrene foam, glass wool, rock wool, and wood may be used. The thermal conductivity of the insulation material 12 on the side of the acoustic element 1 is lower than that of the inner surface of the acoustic element case 29 so that the heat is hardly transferred between the space on the side of the electric signal processing circuit 3 and the acoustic element 1 in the case 9. Accordingly, the transfer of the heat generated from the electric signal processing circuit 3 to the acoustic element 1 can be prevented.

When the size of the through-hole 11 is the size in which the element case lid 31 does not contact with the acoustic element board 2, it is preferable that a gap between the element case lid 31 and the acoustic element board 2 be filled with the insulation material 12. Also, it is preferable that the insulation material 12 be filled so as to contact with both the element case lid 31 and the acoustic element 1. The transfer of the heat generated by the electric signal processing circuit 3 to the acoustic element 1 via the acoustic element board 2 and the case 9 can be prevented by filling the insulation material 12 in this way and forming the element case lid 31 for contacting with the case 9.

Here, in order to arrange the insulation material 12 in a space surrounded by the acoustic element 1, the element case lid 31, and the acoustic element case 29, the opening of the acoustic element case 29 may be covered with the element case lid 31 after the previously-molded insulation material 12 has been placed in the acoustic element case 29. Alternatively, a hole 13 may be provided in the element case lid 31, and the insulation material 12 may be injected from the hole 13. That is, after the opening of the acoustic element case 29 has been covered with the element case lid 31, the insulation material 12 is injected from the hole 13. After the injection of the insulation material 12, the hole 13 is sealed with a lid 14 so as to cover it. Accordingly, the space surrounded by the acoustic element 1, the element case lid 31, and the acoustic element case 29 is surely filled with the insulation material 12 without a gap. At this time, the hole 13 is sealed with the lid 14 in a state where the space on the side of the acoustic element 1 in the case 9 has been filled with the insulation material 12. That is, at least an opening on the side of the acoustic element 1 of the hole 13 is sealed with the insulation material 12.

Figure 15:
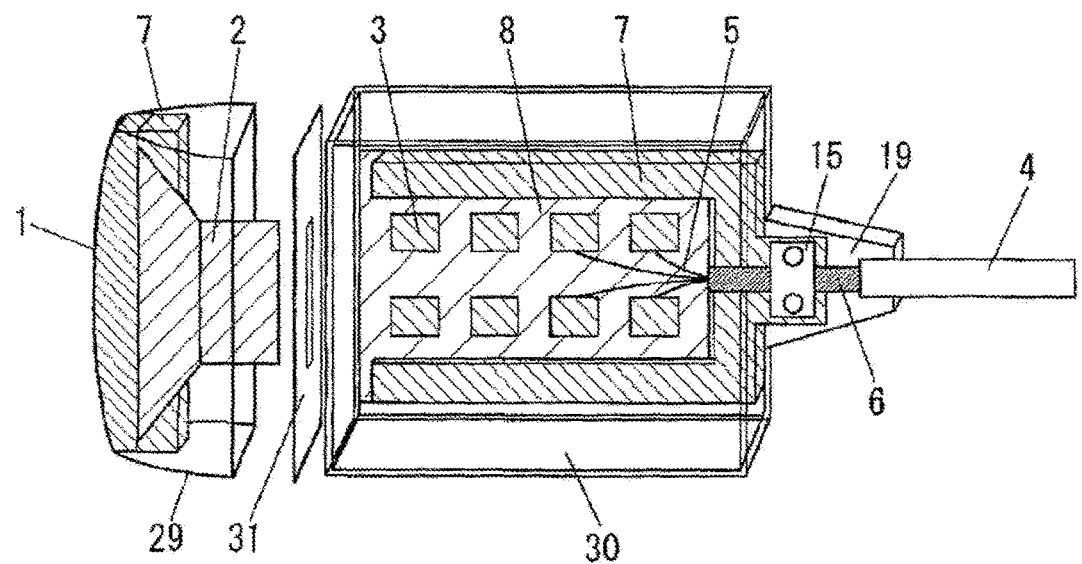
FIG. 15 is a diagram of an example in which a case 9 of the ultrasound probe S according to the second embodiment is separated and three-dimensionally illustrated.
Figure 16:
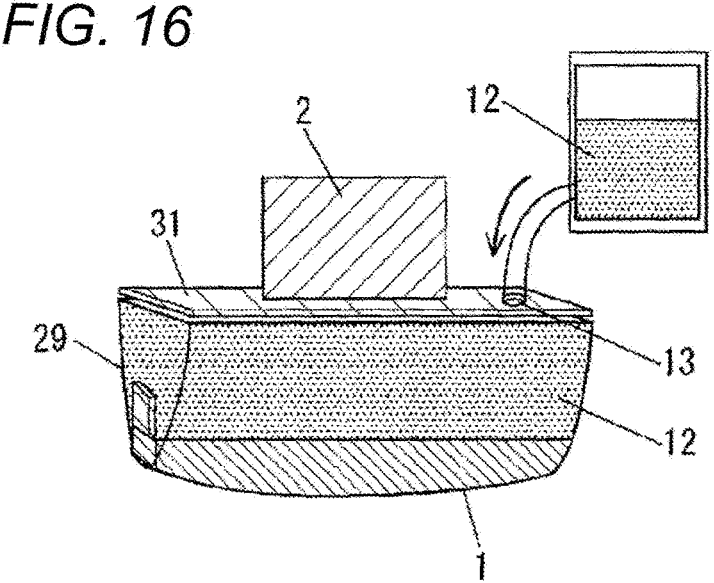
FIG. 16 is a diagram of an exemplary method for filling an insulation material in the case of the ultrasound probe according to the second embodiment.

FIG. 15 is a three-dimensional diagram of the ultrasound probe S according to the second embodiment in which the acoustic element case 29 and the circuit unit case 30 are separated. FIG. 16 is a diagram of a state where the insulation material 12 is injected from the hole 13. As illustrated in FIG. 16, after the acoustic element 1 has been stored in the acoustic element case 29 and the opening of the acoustic element case 29 has been covered with the element case lid 31, the insulation material 12 is injected into the hole 13 of the element case lid 31 which has been previously provided. After the injection of the insulation material 12, the hole 13 is sealed with the lid 14. After that, the acoustic element board 2 and the electric signal processing circuit 3 are electrically connected to each other, and the acoustic element case 29 and the circuit unit case 30 are bonded to each other.

In the space in the case 9 separated by the element case lid 31, the space on the side of the electric signal processing circuit 3 surrounded by the element case lid 31 and the circuit unit case 30 is filled with gas such as air. That is, the electric signal processing circuit 3 contacts with gas.

The circuit unit case 30 has a box shape which opens toward the side of the acoustic element 1 in FIG. 15. However, the shape of the circuit unit case 30 is not limited to this. For example, as the case 9 in the first embodiment, the circuit unit case 30 may include two parts (upper and lower parts), and the electric signal processing circuit 3 may be sandwiched between the two parts from upper and lower sides. In a case of this structure, as described in relation to the first embodiment, since a heat dissipating plate in the case 24 sandwiched between the two parts of the circuit unit case 30 can be easily arranged, the heat generated from the electric signal processing circuit 3 can be efficiently dissipated.

As described above, in the ultrasound probe S according to the second embodiment of the present disclosed technique, the acoustic element 1 and the electric signal processing circuit 3 are spatially separated by the element case lid 31 formed so as to contact with the insulation material 12 and the case 9. Accordingly, the convection of the air between the space on the side of the acoustic element 1 and the space on the side of the electric signal processing circuit 3 in the case 9 can be eliminated, and the transfer of the heat from the electric signal processing circuit 3 to the acoustic element 1 can be prevented. Also, the heat generated by the electric signal processing circuit 3 is efficiently transferred to the cable 4 and the strain relief 19 via an arm 18 for supporting a cable clamp 15.

That is, the ultrasound probe S which can be connected to the ultrasound diagnosis apparatus includes the acoustic element 1 for converting an electric signal and an ultrasound to each other, the electric signal processing circuit 3 electrically connected to the acoustic element 1, the case 9 for storing the acoustic element 1 and the electric signal processing circuit 3, an acoustic element board 2 for electrically connecting the acoustic element 1 to the electric signal processing circuit 3, and the element case lid 31 which is arranged so as to contact with the case 9 and separates the acoustic element 1 and the electric signal processing circuit 3. The space on the side of the acoustic element 1 in the case 9 separated by the element case lid 31 is filled with the first material (insulation material 12) having lower thermal conductivity than that of a material which forms an inner wall surface of the case 9. Accordingly, the heat generated from the electric signal processing circuit 3 which is a heat source can be efficiently dissipated, and the transfer of the heat to the acoustic element 1 can be provided. When having at least these components, the above-mentioned purpose of the present disclosed technique can be achieved.

In the second embodiment, the transfer of the heat generated by the electric signal processing circuit 3 and the like to the acoustic element 1 caused by the convection of the air can be prevented especially in a state where the acoustic element 1 is held upward. Accordingly, since the increase in the temperature of the acoustic element 1 can be reduced, the sensitivity reduction of the ultrasound probe caused by the limitation of the ultrasound output related to the limitation of the surface temperature of the acoustic element 1 can be reduced.

First Modification of Second Embodiment

FIG. 17A is a cross-sectional diagram of an ultrasound probe T according to a first modification of the second embodiment. FIG. 17B is a cross-sectional diagram of the ultrasound probe T in FIG. 17A viewed from an A-A' cross section. Here, the components of the ultrasound probe similar to those described in the first and second embodiments have the same symbols as those of the first and second embodiments, and the detailed description regarding the above components will be omitted.

In the first modification of the second embodiment, three partition plates 32 are further provided. The partition plates 32 are arranged at a predetermined interval relative to the element case lid 31 and with each other and arranged closer to the acoustic element 1 than the element case lid 31. A coupling part 34 passes through each partition plates 32 and the element case lid 31 so that each partition plates 32 and the element case lid 31 are coupled with each other. Each partition plate 32 is arranged so as to contact with the acoustic element case 29 similarly to the element case lid 31. A space between the partition plates 32, a space between the partition plate 32 and the element case lid 31, and a space between the partition plate 32 and the acoustic element 1 are filled with air and are air layers.

More particularly, the element case lid 31 for spatially separating the acoustic element 1 and the electric signal processing circuit 3 is provided between the acoustic element 1 and the electric signal processing circuit 3 in the case 9. The three partition plates 32 are further provided which are formed of the plates arranged at a predetermined interval and arranged closer to the acoustic element 1 than the element case lid 31. Each partition plate 32 is coupled with the element case lid 31 with the coupling part 34. Each partition plate 32 is arranged so as to contact with the acoustic element case 29, and an acoustic element board 2 passes through each partition plate 32 and the element case lid 31. The acoustic element board 2 passes through through-holes 11 provided near the centers of the element case lid 31 and the partition plates 32. It is preferable that the size of the through-hole 11 be a size in which the partition plate 32 and the element case lid 31 contact with the acoustic element board 2. However, the size is not limited to this, and there may be a gap in which the heat transfer caused by the convection of the air via the through-hole 11 is a negligible degree. In addition, the through-hole 11 through which the acoustic element board 2 has passed can be sealed with the adhesive and the like.

Here, three partition plates 32 are formed. However, it is preferable that the number of the partition plates 32 be at least one or more. For example, the partition plate 32 may be formed of the same material as that of the element case lid 31 or the acoustic element case 29. When the opening of the acoustic element case 29 is covered with the element case lid 31, the partition plates 32 coupled with the element case lid 31 can be concurrently stored in the acoustic element case 29 at a constant interval by coupling the element case lid 31 with the partition plate 32 by the coupling part 34.

In this way, the space in the case 9 is divided by the element case lid 31 and the partition plate 32, and air layers are respectively provided in the divided spaces. Accordingly, even when the insulation material other than air is not arranged in the case 9, the transfer of the heat from the electric signal processing circuit 3 to the acoustic element 1 can be prevented.

Second Modification of Second Embodiment

FIG. 18A is a cross-sectional diagram of an ultrasound probe U according to a second modification of the second embodiment. FIG. 18B is a cross-sectional diagram of the ultrasound probe U in FIG. 18A viewed from an A-A' cross section. Here, the components of the ultrasound probe similar to those described in the first and second embodiments have the same symbols as those in the first and second embodiments, and the detailed description of those will be omitted.

In the second modification of the second embodiment, a single partition plate 33, which is formed of a plate arranged at a predetermined interval relative to the element case lid 31 and arranged closer to the acoustic element 1 than the element case lid 31, is further provided. The coupling part 34 passes through the partition plate 33 and the element case lid 31 so that the partition plate 33 and the element case lid 31 are coupled with each other. The partition plate 33 is arranged so as to contact with the acoustic element case 29 similarly to the element case lid 31. In addition, the insulation material 27 is arranged between the partition plate 33 and the element case lid 31. The insulation material 27 is arranged so as to contact with the surfaces of the partition plate 33 and the element case lid 31 facing to each other and the acoustic element case 29. Also, the high thermal conductive material 28 having higher high thermal conductivity than that of the insulation material 27 is arranged in a space between the acoustic element 1 and the partition plate 33.

More particularly, the acoustic element board 2 passes through the element case lid 31 and the partition plate 33. The acoustic element board 2 passes through the through-holes 11 provided near the centers of the partition plate 33 and the element case lid 31. It is preferable that the size of the through-hole 11 be a size in which the element case lid 31 and the partition plate 33 contact with the acoustic element board 2.

For example, the partition plate 33 may be formed of the same material as that of the element case lid 31 or the acoustic element case 29. When the opening of the acoustic element case 29 is covered with the element case lid 31, the partition plate 33 coupled with the element case lid 31 can be concurrently stored in the acoustic element case 29 at a constant interval by coupling the element case lid 31 with the partition plate 33 by the coupling part 34.

The insulation material 27 may be, for example, rigid urethane foam, expanded polystyrene foam, glass wool, rock wool, air, and wood. The high thermal conductive material 28 may be, for example, a mixture of a resin such as a PBT resin, a PPS resin, a nylon resin, and a phenol resin into a filler such as silicon carbide, aluminum nitride, boron nitride, magnesium oxide, aluminum oxide, and aluminum nitride.

Figure 19:
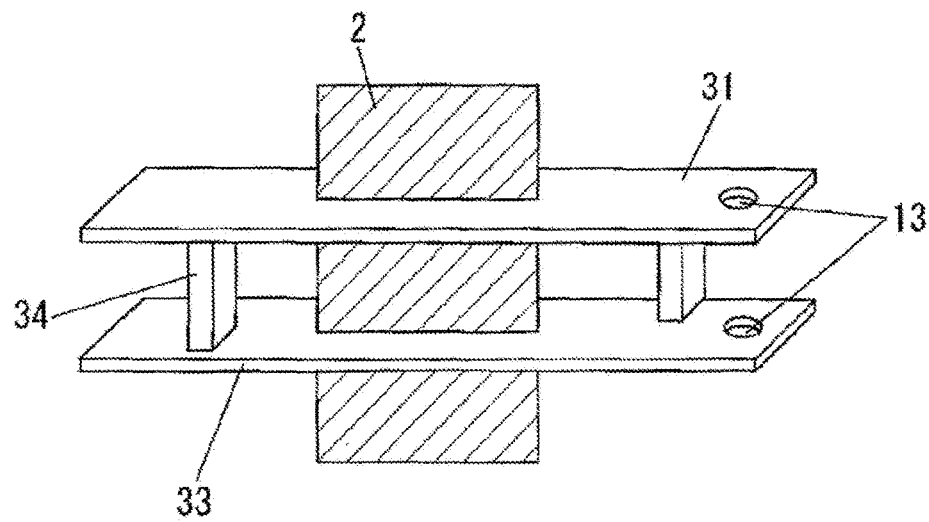
FIG. 19 is a diagram to describe an exemplary part of the ultrasound probe U.
Figure 20:
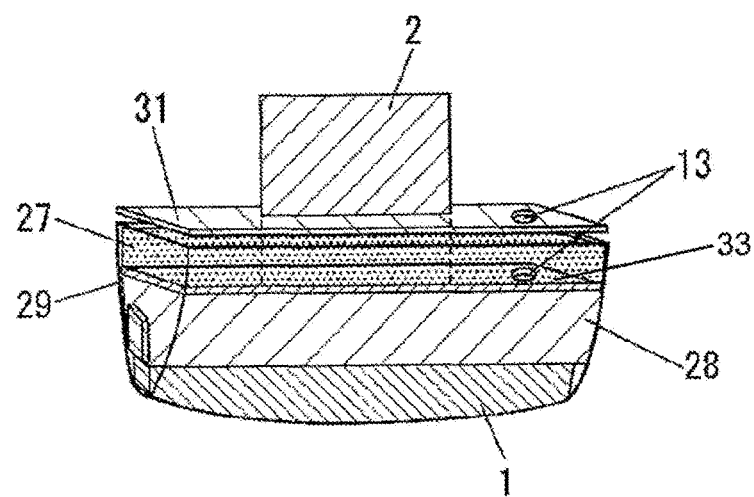
FIG. 20 is a diagram of an exemplary method for filling an insulation material in a case of the ultrasound probe U.
Figure 22:
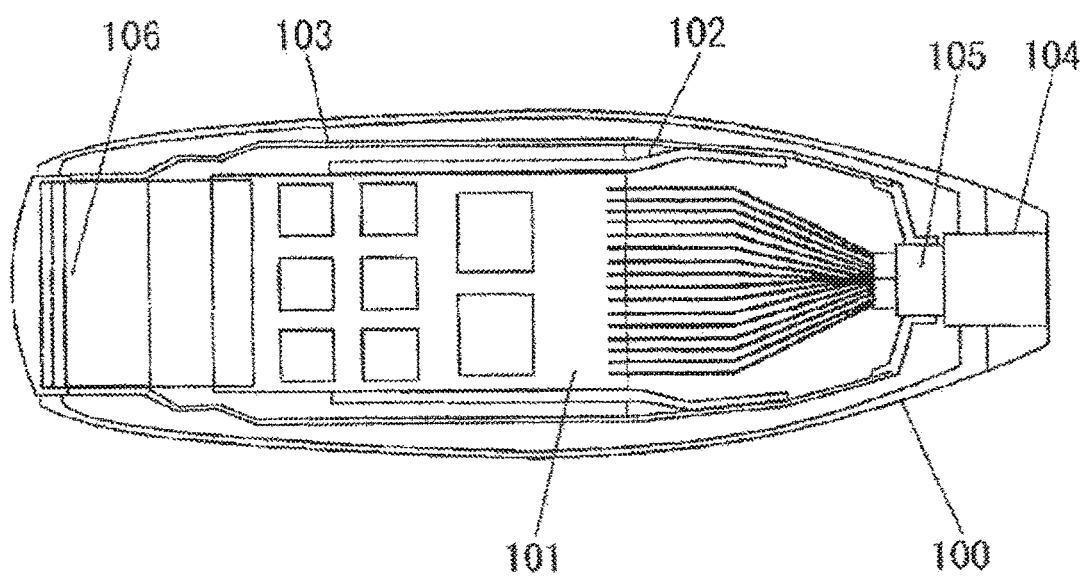
FIG. 22 is a diagram of a conventional example.

In order to arrange the insulation material 27 and the high thermal conductive material 28, the high thermal conductive material 28, the partition plate 33, the insulation material 27, and the element case lid 31 may be arranged in this order after the acoustic element 1 has been stored in the acoustic element case 29. Alternatively, as illustrated in FIG. 19, the insulation material 27 and the high thermal conductive material 28 may be arranged in the acoustic element case 29 by using the holes 13 respectively provided in the partition plate 33 and the element case lid 31. Specifically, the acoustic element 1 is stored in the acoustic element case 29, and the partition plate 33 and the element case lid 31 are arranged so as to cover the opening of the acoustic element case 29. After that, as illustrated in FIG. 20, the high thermal conductive material 28 is injected into the space between the acoustic element 1 and the partition plate 33 from the holes 13. The injected high thermal conductive material 28 is cooled and solidified. Next, the insulation material 27 is injected into the space between the partition plate 33 and the element case lid 31 from the holes 13. A space surrounded by the acoustic element 1, the partition plate 33, and the acoustic element case 29 can be surely filled with the high thermal conductive material 28 without a gap by arranging the high thermal conductive material 28 and the insulation material 27 according to this method. Also, a space surrounded by the partition plate 33, the element case lid 31, and the acoustic element case 29 can be surely filled with the insulation material 27 without a gap. In addition, the holes 13 formed in the partition plate 33 and the element case lid 31 may be respectively sealed with lids. After that, the acoustic element case 29 is bonded to the circuit unit case 30.

The insulation material 27 may be, for example, rigid urethane foam, expanded polystyrene foam, glass wool, rock wool, air, and wood. The high thermal conductive material 28 may be, for example, a mixture of a resin such as a PBT resin, a PPS resin, a nylon resin, and a phenol resin into a filler such as silicon carbide, aluminum nitride, boron nitride, magnesium oxide, aluminum oxide, and aluminum nitride.

According to the second modification of the second embodiment, the insulation material 27 is arranged between the element case lid 31 and the partition plate 33, and the high thermal conductive material 28 is arranged between the acoustic element 1 and the partition plate 33. With this arrangement, the transfer of the heat generated by the electric signal processing circuit 3 to the acoustic element 1 can be prevented by the insulation material 27. In addition, since the heat generated by the acoustic element 1 is transferred to the acoustic element case 29 via the high thermal conductive material 28 by the high thermal conductive material 28, the heat can be dissipated. Accordingly, since the increase in the surface temperature of the acoustic element 1 can be reduced, the sensitivity reduction of the ultrasound probe caused by the limitation of the ultrasound output related to the limitation of the surface temperature of the acoustic element 1 can be reduced.

Third Modification of Second Embodiment

FIG. 21A is a cross-sectional diagram of an ultrasound probe V according to a third modification of the second embodiment. FIG. 21B is a cross-sectional diagram of the ultrasound probe V in FIG. 21A viewed from an A-A' cross section. Here, the components of the ultrasound probe similar to those described in the first and second embodiments have the same symbols as those of the first and second embodiments, and the detailed description regarding the above components will be omitted.

In the third modification of the second embodiment, the element case lid 31 is sandwiched between the acoustic element case 29 and the circuit unit case 30. That is, the element case lid 31 is formed on a plane including a bonding surface of the acoustic element case 29 and the circuit unit case 30. Accordingly, the acoustic element case 29 is connected to the circuit unit case 30 via the element case lid 31 without directly contacting with each other. That is, the element case lid 31 extends to the bonding part of the acoustic element case 29 and the circuit unit case 30. The element case lid 31 is formed of a material having lower thermal conductivity (for example, a modified PPE resin) than those of the acoustic element case 29 and the circuit unit case 30.

With this structure, the element case lid 31 with low thermal conductivity intervenes between the acoustic element case 29 and the circuit unit case 30 formed of a material with high thermal conductivity, and the acoustic element case 29 does not directly contact with the circuit unit case 30. Therefore, the transfer of the heat between the acoustic element case 29 and the circuit unit case 30 can be prevented. Especially, when the power consumption of the electric signal processing circuit 3 increases, the increase in the temperature of the circuit unit case 30 becomes larger than that of the acoustic element case 29. In this case, when the transfer of the heat from the circuit unit case 30 to the acoustic element case 29 can be prevented by providing the element case lid 31, the increase in the surface temperature of the acoustic element 1 can be reduced. Therefore, the sensitivity reduction of the ultrasound probe caused by the limitation of the ultrasound output related to the limitation of the surface temperature of the acoustic element 1 can be reduced.

The third modification of the second embodiment can be appropriately combined with the first or second modifications of the second embodiment. That is, for example, the acoustic element case 29 may be bonded to the circuit unit case 30 by arranging the partition plate 32 (first modification) and the partition plate 33 (second modification) so as to contact with the inner wall of the acoustic element case 29 and arranging the element case lid 31 so as to be sandwiched between the acoustic element case 29 and the circuit unit case 30 as in the third modification.

According to the present disclosed technique, the convection of the air between the acoustic element 1 and the circuit unit (electric signal processing circuit 3) which is a heat generation source in the case of the ultrasound probe can be prevented, and the heat from the circuit unit can be efficiently dissipated. Therefore, the present disclosed technique is especially suitable for the ultrasound probe having the circuit unit which is the heat generation source in the case.

The invention claimed is:

1. An ultrasound probe for connecting to an ultrasound diagnosis apparatus, comprising:
    an acoustic element configured to convert an electric signal and an ultrasound to each other;
    an electric signal processing circuit configured to be electrically connected to the acoustic element;
    a case configured to store the acoustic element and the electric signal processing circuit;
    an acoustic element board configured to electrically connect the acoustic element to the electric signal processing circuit;
    a partition part configured to be arranged so as to contact with the case and separate the acoustic element and the electric signal processing circuit;
    a circuit unit board configured to include the electric signal processing circuit mounted on the circuit unit board;
    a cable configured to electrically connect the electric signal processing circuit to the ultrasound diagnosis apparatus and transfer a signal; and
    at least one arm configured to be connected to the cable and support the circuit unit board,
    wherein:
    a space on a side of the acoustic element in the case separated by the partition part is filled with a first material having lower thermal conductivity than that of a material for forming an inner wall surface of the case,
    the electric signal processing circuit contacts with gas, and
    the arm has higher thermal conductivity than that of the first material.

2. The ultrasound probe according to claim 1, wherein:
    the arm is formed of a conductive material, and
    the circuit unit board includes a ground electrode of the electric signal processing circuit in a contact part with the arm.

3. The ultrasound probe according to claim 1, further comprising:
    a cable clamp configured to fix the cable,
    wherein the cable is connected to the arm via the cable clamp.

4. The ultrasound probe according to claim 3, wherein the cable clamp is connected to a heat dissipating plate arranged to surround the cable.

5. The ultrasound probe according to claim 4, further comprising:
    a strain relief configured to be penetrated by the cable outside the case and contact with the case,
    wherein the heat dissipating plate includes a first heat dissipating plate arranged between the case and the cable and a second heat dissipating plate arranged in the strain relief and for contacting with the first heat dissipating plate.

6. The ultrasound probe according to claim 3, wherein the cable clamp and the arm are integrally formed.

7. The ultrasound probe according to claim 3, wherein:
    the arm is formed of metal, and
    oxidation treatment or heat radiating coating is performed to a surface of the arm on the side of the cable clamp from the center in a longitudinal direction.

8. The ultrasound probe according to claim 1, wherein:
    the case includes at least first and second parts, and
    the first and second parts are bonded to each other.

9. The ultrasound probe according to claim 8, wherein the first and second parts respectively cover from the acoustic element to the electric signal processing circuit.

10. The ultrasound probe according to claim 8, wherein the partition part is integrally formed with the first part.

11. The ultrasound probe according to claim 8, wherein:
    the first part stores the acoustic element,
    the second part stores the electric signal processing circuit, and
    the first and the second parts are bonded between the acoustic element and the electric signal processing circuit.

12. The ultrasound probe according to claim 11, wherein the partition part is formed on a plane of a bonding surface of the first and second parts.

13. The ultrasound probe according to claim 11, wherein:
    a first hole through which the acoustic element board passes and a second hole different from the first hole are formed in the partition part, and
    an opening on the side of the acoustic element of the second hole is sealed with the first material in a state where a space on the side of the acoustic element in the case has been filled with the first material.

14. The ultrasound probe according to claim 11, wherein the partition part is sandwiched between the first and second parts on the bonding surface of the first and second parts.

15. The ultrasound probe according to claim 8, wherein the first part has higher thermal conductivity than that of the partition part.

16. The ultrasound probe according to claim 1, wherein:
    a hole is formed in a part positioned between the partition part and the acoustic element in the case, and
    an opening on the side of the acoustic element of the hole is sealed with the first material in a state where a space on the side of the acoustic element in the case has been filled with the first material.

17. The ultrasound probe according to claim 1, wherein the partition part includes at least two or more partition plates.

18. The ultrasound probe according to claim 17, wherein in the at least two or more partition plates, a space between the at least two or more partition plates is filled with the first material, and a space between the acoustic element and the partition plate is filled with a second material with higher thermal conductivity than that of the first material.

19. The ultrasound probe according to claim 1, wherein a graphite layer is formed on an inner wall surface of the case.

20. The ultrasound probe according to claim 1, wherein:
    the case is formed of resin containing a filler,
    the resin is one of a PBT resin, a PPS resin, a nylon resin, and a phenol resin, and
    the filler is one of silicon carbide, aluminum nitride, boron nitride, magnesium oxide, aluminum oxide, and aluminum nitride.

21. The ultrasound probe according to claim 20, wherein the case has thermal conductivity of 2 to 15 W/m·K.

* * * * *